United States Patent [19]

Chu et al.

[11] Patent Number: 4,880,814
[45] Date of Patent: Nov. 14, 1989

[54] 7-CYCLOALKYL NAPHTHYRIDINES

[75] Inventors: Daniel T. Chu, Vernon Hills; Terry J. Rosen, Deerfield; Curt S. Cooper, Lake Bluff, all of Ill.

[73] Assignee: Abbott Laboratories, Abbott Park, Ill.

[21] Appl. No.: 119,885

[22] Filed: Nov. 13, 1987

[51] Int. Cl.$^4$ .................. C07D 471/04; A61K 31/44
[52] U.S. Cl. .................... 514/300; 546/123; 546/156; 546/81; 546/82; 546/83; 546/80; 514/292; 514/293; 514/312; 514/291
[58] Field of Search ...................... 546/123; 514/300

[56] References Cited

U.S. PATENT DOCUMENTS 3,590,036  6/1971  Lesher et al. ..................... 546/123
4,571,396  2/1986  Hutt et al. ....................... 546/123

Primary Examiner—Jane T. Fan
Attorney, Agent, or Firm—Steven F. Weinstock; Edward H. Gorman, Jr.

[57] ABSTRACT

The present invention includes compounds represented by the formula:

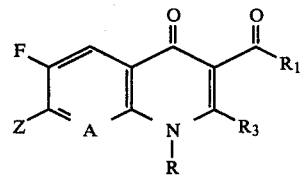

wherein $R_1$ is a hydroxy, a $C_1$ to $C_6$ alkoxy, benzoxy, or an alkylcarbonyloxymethoxy group, or $R_3$ together with $R_1$ forms a group of the formula —Y—NH— where Y is oxygen or sulfur; or $R_3$ is hydrogen; A is nitrogen or $CR_2$, where $R_2$ is hydrogen, or halogen, or $R_2$ together with R forms a group of the formula —X—$CH_2$—$CH(R_6)$— or —X—$CH_2$—CH=$CH_2$, wherein X is $CH_2$, O, S, NH, or $NCH_3$, and $R_6$ is hydrogen, alkyl, or $C_1$-$C_3$ haloalkyl; or R is (1) a $C_1$ to $C_4$ alkyl, (2) lower cycloalkyl, (3) alkylamino, (4) haloalkyl, (5) an aromatic heterocyclic ring or (6) a substituted phenyl group; and Z is a carbocyclic group;

or a pharmaceutically acceptable salt thereof. The compounds of the present invention are useful as antibacterial agents. 1

7 Claims, No Drawings

7-CYCLOALKYL NAPHTHYRIDINES

TECHNICAL FIELD

This invention relates to new quinoline and naphthyridine derivatives having antibacterial properties, compositions containing the new quinoline derivatives and methods of treating mammalian patients with the new quinoline derivatives.

BACKGROUND ART

It is known that certain quinoline compounds exhibit antibacterial properties, notably certain 7-piperazinyl-4-oxo-1,4-dihydroquinoline-3-carboxylic acids. In U.S. Pat. No. 4,017,622, there are disclosed certain 7-piperazinyl-4-oxo-1,4-dihydroquinoline-3-carboxylic acids derivatives which are substituted in the 1 position with an alkyl, benzyl or acetyl substituent. U.S. Pat. No. 4,292,317 discloses derivatives of 7-piperazinyl-4-oxo-1,4-dihydroquinoline-3-carboxylic acids wherein the 1 position is substituted by an alkyl group or a vinyl group. In U.S. Pat. No. 4,284,629, there are disclosed various 4-oxo-1,4-dihydroquinoline-3-carboxylic acids in which the 1 position is substituted with a cycloalkyl group.

It is also known that certain naphthyridine compounds exhibit antibacterial properties, notably certain 7-piperazinyl-4-oxo-1,8-naphthyridine-3-carboxylic acids. In European Patent No. 9,425, there are disclosed certain 7-piperazinyl-6-fluoro-1,4-dihyro-4-oxo-1,8-naphthyridine-3-carboxylic acids derivatives which are substituted in the 1 position with an alkyl or vinyl substituent. U.S. Pat. No. 4,616,019 discloses derivatives of 7-substituted-amino-4-oxo-1,4-dihydro-1,8-naphthyridine-3-carboxylic acids derivatives which are substituted in the 1 position with an aromatic group such as substituted phenyl.

DISCLOSURE OF THE INVENTION

This invention relates to novel quinoline, naphthyridine, benzoxazine, isoxazolo-quinoline, isoxazolo-naphthyridine, isothiazolo-quinoline and isothiazolo-naphthyridine derivatives having antibacterial properties.

More particularly, this invention relates to compounds having the formula

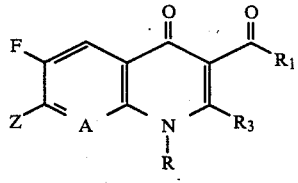
(I)

wherein $R_1$ is a hydroxy, a $C_1$ to $C_6$ alkoxy, benzoxy, or an alkylcarbonyloxymethoxy group, or $R_3$ together with $R_1$ forms a group of the formula —Y—NH— where Y is oxygen or sulfur; or $R_3$ is hydrogen; A is nitrogen or $CR_2$, where $R_2$ is hydrogen, or halogen, or $R_2$ together with R forms a group of the formula —X—$CH_2$—$CH(R_6)$— or

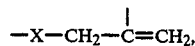

wherein X is $CH_2$, O, S, NH, or $NCH_3$, and $R_6$ is hydrogen, alkyl, or $C_1$–$C_3$ haloalkyl; or R is (1) a $C_1$ to $C_4$ alkyl, (2) lower cycloalkyl, (3) alkylamino, (4) haloalkyl, (5) an aromatic heterocyclic ring having 5 to 6 atoms with the hetero atom being at least one of O, N and S and the remaining atoms being carbon atoms, the aromatic heterocyclic group being unsubstituted or substituted with a halogen or $C_1$–$C_4$ alkyl, or (6) a phenyl group of the formula:

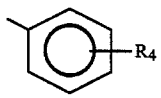

wherein $R_4$ is one, two or three substituents independently selected from hydrogen, halogen, $C_1$ to $C_4$ alkyl, methylenedioxy, and a group of the formula $OR_5$, wherein $R_5$ is hydrogen or $C_1$ to $C_5$ alkyl; and Z is a carbocyclic group of the formula:
where n is 1 or 2, and $R_7$ is one or more of (1) hydrogen, (2) halogen, (3) loweralkyl, (4) oxo, (5) cyano, (6) alkanoylamino, (7) carboxyl, (8) nitro, (9) haloalkyl, (10) phenyl, (11) a substituted phenyl of the formula:

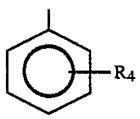

(12) an amine having the formula:

(13) an aminoalkyl group having the formula:
wherein, m is 1 to 4, and $R_8$ and $R_9$ are independently selected from hydrogen, $C_1$ to $C_4$ alkyl, alkylamino, hydroxy substituted $C_1$ to $C_4$ alkyl, and amino; or (14) an imine of the formula:

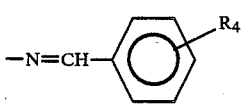

or a pharmaceutically acceptable salt thereof.

As used herein, the term "halogen" refers to chloro, bromo, fluoro and iodo groups.

The term "loweralkyl" refers to straight or branched chain alkyl groups containing from 1 to 7 carbon atoms.

The term "$C_1$ to $C_4$ alkyl" refers to branched or straight chain lower alkyl groups including but not limited to methyl, ethyl, propyl, isopropyl, butyl, and the like.

The terms "halo-substituted alkyl" or "haloalkyl" refer to halogen substituted $C_1$ to $C_4$ alkyl including but not limited to a fluoroethyl group.

The term "lowercycloalkyl" refers to $C_3$ to $C_6$ cycloalkyl groups including but not limited to cyclopropyl, cyclobutyl, cyclopentyl and cyclohexyl group.

The term "amino" refers to —$NH_2$.

The term "alkylamino" refers to a mono- or di-substituted amino group substituted with $C_1$ to $C_4$ alkyl including but not limited to methylamino and ethylmethylamino.

The term "alkanoylamino" refers to a substituent of the formula $R_{10}CONH-$ wherein $R_{10}$ is $C_1$ to $C_3$ alkyl, and includes but is not limited to acetylamino.

The term "alkylcarbonyloxymethoxy" refers to a group of formula $-OCH_2-O-C(O)-R_a$ where $R_a$ is a straight or branched $C_1$ to $C_6$ alkyl, including a pivaloyoxymethoxy group.

The preferred compounds of the invention are those having the formula:

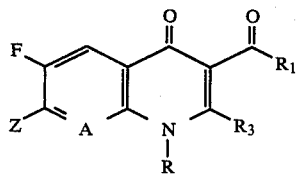

wherein R is ethyl, cyclopropyl, phenyl or substituted phenyl wherein the substituent on the phenyl group is one or more of halogen, methylenedioxy or hydroxy. A and $R_2$ and $R_3$ are defined as above; $R_1$ is OH; or $R_1$ and $R_3$ taken together are isoxazolo or isothiazolo rings as defined above; $R_2$ and R taken together is benzoxazine as defined above; Z is 3-aminocyclopentyl or substituted cyclopentyl or 4-aminocyclohexyl or substituted 4-aminocyclohexyl or substituted 3-aminomethylcyclopentyl or substituted 4-aminomethyl cyclopentyl as described.

The chiral centers of the compounds of the invention may have either the "R" or "S" configuration.

Representative of such preferred compounds wherein $R_1$ is hydroxy, $R_3$ is hydrogen, A is $CR_2$ or nitrogen, and $R_2$ is H, F, or Cl are 1-cyclopropyl-6-fluoro-1,4-dihydro-4-oxo-7-(4-aminocyclohexyl)-quinoline-3-carboxylic acid, 1-o,p-difluorophenyl-6-fluoro-1,4-dihydro-4-oxo-7-(4-ethylaminocyclohexyl)-quinoline-3-carboxylic acid, 1-o,p-difluorophenyl-6-fluoro-1,4-dihydro-4-oxo-7(3-aminocyclopentyl)-quinoline-3-carboxylic acid, 1-o,p-difluorophenyl-6-fluoro-1,4-dihydro-4-oxo-7-(4-aminocyclohexyl)-quinoline-3-carboxylic acid, 1-cyclopropyl-6-fluoro-1,4-dihydro-4-oxo-7-(3-aminocyclopentyl)-quinoline-3-carboxylic acid, 1-cyclopropyl-6-fluoro-1,4-dihydro-4-oxo-7-(3-ethylaminomethyl-1-cyclopentyl)-quinoline-3-carboxylic acid, 1-ethyl-6-fluoro-1,4-dihydro-4-oxo-7-(4-aminocyclopentyl)-quinoline-3-carboxylic acid, 1-p-fluorophenyl-6-fluoro-1,4-dihydro-4-oxo-7-(4-aminocyclohexyl)-quinoline-3-carboxylic acid, 1-cyclopropyl-6-fluoro-1,4-dihydro-4-oxo-7-(4-aminocyclohexyl)-1,8-naphthyridine-3-carboxylic acid, 1-cyclopropyl-6-fluoro-7-(3-aminocyclopentyl)-1,4-dihydro-4-oxo-1,8-naphthyridine-3-carboxylic acid, 1-cyclopropyl-6-fluoro-(3-ethylaminomethylcyclopentyl)-1,4-dihydro-4-oxo-1,8-naphthyridine-3-carboxylic acid, 1-ethyl-6-fluoro-7-(3-aminocyclopentyl)-1,4-dihydro-4-oxo-1,8-naphthyridine-3-carboxylic acid, 1-ethyl-6-fluoro-7-(4-aminocyclohexyl)-1,4-dihydro-4-oxo-1,8-naphthyridine-3-carboxylic acid, 1-o,p-difluorophenyl-6-fluoro-7-(3-aminocyclopentyl)-1,4-dihydro-4-oxo-1,8-naphthyridine-3-carboxylic acid, 1-cyclopropyl-6,8-difluoro-1,4-dihydro-4-oxo-7-(4-aminocyclohexyl)-quinoline-3-carboxylic acid, 1-o,p-difluorophenyl-6,8-difluoro-1,4-dihydro-4-oxo-7-(4-methylaminocyclohexyl)-quinoline-3-carboxylic acid, 1-o,p-difluorophenyl-6,8-difluoro-1,4-dihydro-4-oxo-7-(3-aminocyclopentyl)-quinoline-3-carboxylic acid, 1-cyclopropyl-6,8-difluoro-1,4-dihydro-4-oxo-7-(3-aminocyclopentyl)-quinoline-3-carboxylic acid, 1-cyclopropyl-6,8-difluoro-1,4-dihydro-4-oxo-7-(3-ethylaminomethylcyclopentyl)-quinoline-3-carboxylic acid, 1-ethyl-6,8-difluoro-1,4-dihydro-4-oxo-7-(3-aminocyclopentyl)-quinoline-3-carboxylic acid, 1-ethyl-6,8-difluoro-1,4-dihydro-4-oxo-7-(3-ethylaminomethyl-1-cyclopentyl)-quinoline-3-carboxylic acid, 1-ethyl-6,8-difluoro-1,4-dihydro-4-oxo-7-(4-aminocyclohexyl)-quinoline-3-carboxylic acid, 1-cyclopropyl-6-fluoro-7-(3aminocyclopentyl)-8-chloro-1,4-dihydro-4-oxo-quinoline-3-carboxylic acid, 1-o,p-difluorophenyl-6-fluoro-7-(3-aminocyclopentyl)-8-chloro-1,4-dihydro-4-oxo-quinoline-3-carboxylic acid, 1-ethyl6-fluoro-7-(3-aminocylcopentyl)-8-chloro-1,4-dihydro-4-oxo-quinoline-3-carboxylic acid.

Other preferred compounds of the invention wherein $R_3$ and $R_1$ when taken together have the formula $$-Y-NH-$$

wherein Y is O or S; and A is N or $CR_2$, $R_2$ is H, F, or Cl are 9-ethyl-6-fluoro-7-(3-aminocyclopentyl)-2,3,4,9-tetrahydroisoxazolo[5,4-b] [1,8]-naphthyridine-3,4-dione, 9-ethyl-6-fluoro-7-(4-aminocyclohexyl)-2,3,4,9-tetrahydroisoxazolo[5,4-b] [1,8]-naphthyridine-3,4-dione, 9-ethyl-6-fluoro-7-(3-ethylaminomethylcyclopentyl)-2,3,4,9-tetrahydroisoxazolo[5,4-b] [1,8]-naphthyridine-3,4-dione, 9-cyclopropyl-6-fluoro-7-(3-aminocyclopentyl)-2,3,4,9-tetrahydroisoxazolo[5,4-b] [1,8]-naphthyridine-3,4-dione, 9-cyclopropyl-6-fluoro-7-(4-aminocyclohexyl)-2,3,4,9-tetrahydroisoxazolo[5,4-b] [1,8]-naphthyridine-3,4 -dione, 9-p-fluorophenyl-6-fluoro-7-(3-aminocyclopentyl)2,3,4,9-tetrahydroisoxazolo[5,4-b] [1,8]-naphthyridine-3,4-dione, 9-p-fluorophenyl-6-fluoro-7-(4-aminocyclohexyl)-2,3,4,9-tetrahydroisoxazolo[5,4-b] [1,8]-naphthyridine-3,4-dione, 9-o,p-difluorophenyl-6-fluoro-7-(3-aminocyclohexyl)-2,3,4,9-tetrahydroisoxazolo[5,4-b] [1,8]-naphthyridine-3,4-dione, 9-o,p-difluorophenyl-6-fluoro-7-(3-aminocyclopentyl)-2,3,4,9-tetrahydroisoxazolo[5,4-b] [1,8]naphthyridine-3,4-dione, 9-ethyl-6-fluoro-7-(4-aminocyclohexyl)-2,3,4,9-tetrahydroisoxazolo[5,4-b]quinoline-3,4-dione, 9-ethyl-6-fluoro-7-(3-aminocyclopentyl)-2,3,4,9-tetrahydroisoxazolo[5,4-b]quinoline-3,4-dione, 9-ethyl-6-fluoro-7-(3-aminocyclohexyl)-2,3,4,9-tetrahydroisoxazolo[5,4-b]quinoline-3,4-dione, 9-cyclopropyl-6-fluoro-7-(3-aminocyclopentyl)-2,3,4,9-tetrahydroisoxazolo[5,4-b]quinoline-3,4-dione, 9-cyclopropyl-6-fluoro-7-(3-aminocyclohexyl)-2,3,4,9-tetrahydroisoxazolo[5,4-b]quinoline-3,4-dione, 9-cyclopropyl-6-fluoro-7-(4-aminocyclohexyl)-2,3,4,9-tetrahydroisoxazolo[5,4-b]quinoline-3,4-dione, 9-p-fluorophenyl-6-fluoro-7-(3-aminocyclohexyl)-2,3,4,9-tetrahydroisoxazolo[5,4-b]quinoline-3,4-dione, 9-p-fluorophenyl-6-fluoro-7-(3-aminocyclopentyl)-2,3,4,9-tetrahydroisoxazolo[5,4-b]quinoline-3,4-dione, 9-o,p-difluorophenyl-6-fluoro-7-(3-aminocyclopentyl)-2,3,4,9-tetrahydroisoxazolo[5,4-b]quinoline-3,4-dione, 9-o,p-difluorophenyl-6-fluoro-7-(3-aminocyclohexyl)-2,3,4,9-tetrahydroisoxazolo[5,4-b]quinoline-3,4-dione, 9-ethyl-6,8-difluoro-7-(3-aminocyclopentyl)2,3,4,9-tetrahydroisoxazolo[5,4-b]quinoline-3,4-dione, 9-ethyl-6,8-difluoro-7-(3-aminocyclohexyl)-2,3,4,9-tetrahydroisoxazolo[5,4-b]quinoline-3,4-dione, 9-ethyl-6,8- difluoro-7-(3-ethylaminomethylcyclopentyl)-2,3,4,9-tetrahydroisoxazolo[5,4-b]quinoline-3,4-dione, 9-cyclopropyl-6,8-difluoro-7-(3-aminocyclopentyl)-2,3,4,9-tetrahydroisoxazolo[5,4-b]quinoline-3,4-dione, 9-cyclopropyl-6,8-difluoro-7-(4-aminocyclohexyl)-2,3,4,9-tetrahydroisoxazolo[5,4-b]quinoline-3,4-dione, 9-cyclopropyl-6,8-difluoro-7-(3-ethylaminomethylcyclopentyl)-2,3,4,9-tetrahydroisoxazolo[5,4-b]quinoline-3,4-dione, 9-p-fluorophenyl-6,8-difluoro-7-(3-aminocyclopentyl)-2,3,4,9-tetrahydroisoxazolo[5,4-b]quinoline-3,4-dione, 9-ethyl-6-fluoro-7-(3-aminocyclopentyl)-2,3,4,9-tetrahydroisothiazolo[5,4-b][1,8]-naphthyridine-3,4-dione, 9-cyclopropyl-6-fluoro-7-(3-aminocyclopentyl)-2,3,4,9-tetrahydroisothiazolo[5,4-b][1,8]-naphthyridine-3,4-dione, 9-cyclopropyl-6-fluoro-7-(4-aminocyclohexyl)-2,3,4,9-tetrahydroisothiazolo[5,4-b][1,8]-naphthyridine-3,4-dione, 9-cyclopropyl-6-fluoro-7-(3-aminocyclohexyl)-2,3,4,9-tetrahydroisothiazolo[5,4-b][1,8]-naphthyridine-3,4-dione, 9-p-fluorophenyl-6-fluoro-7(3-aminocyclopentyl)-2,3,4,9-tetrahydroisothiazolo[5,4-b][1,8]-naphthyridine-3,4-dione, 9-o,p-difluorophenyl-6-fluoro-7-(3-aminocyclopentyl)-2,3,4,9-tetrahydroisothiazolo[5,4-b][1,8]-naphthyridine-3,4-dione, 9-ethyl-6-fluoro-7-(3-aminocyclopentyl)-2,3,4,9-tetrahydroisothiazolo[5,4-b]quinoline-3,4-dione, 9-ethyl-6-fluoro-7-(4-aminocyclohexyl)-2,3,4,9-tetrahydroisothiazolo[5,4-b]quinoline-3,4-dione-, 9-cyclopropyl-6-fluoro-7-(3-aminocyclopentyl)-2,3,4,9-tetrahydroisothiazolo[5,4-b]quinoline-3,4-dione, 9-cyclopropyl-6-fluoro-7-(3-ethylaminomethylcyclopentyl)-2,3,4,9-tetrahydroisothiazolo[5,4-b]quinoline-3,4-dione, 9-cyclopropyl-6-fluoro-7-(3-aminocyclopentyl)-8-chloro-2,3,4,9-tetrahydroisothiazolo[5,4-b]quinoline-3,4-dione, 9-cyclopropyl-6-fluoro-7-(4-aminocyclohexyl)-8-chloro-2,3,4,9-tetrahydroisothiazolo[5,4-b]quinoline-3,4-dione, 9-ethyl-6-fluoro-7-(3-aminocyclopentyl)-8-chloro-2,3,4,9-tetrahydroisothiazolo[5,4-b]quinoline-3,4-dione, 9-p-fluorophenyl-6-fluoro-7-(3-aminocyclopentyl)-2,3,4,9-tetrahydroisothiazolo[5,4-b]quinoline-3,4-dione, 9-o,p-difluorophenyl-6-fluoro-7-(3-aminocyclopentyl)-2,3,4,9-tetrahydroisothiazolo[5,4-b]quinoline-3,4-dione, 9-ethyl-6,8-difluoro-7-(3-aminocyclopentyl)-2,3,4,9-tetrahydroisothiazolo[5,4-b]quinoline-3,4-dione, 9-ethyl-6,8-difluoro-7-(4-aminocyclohexyl)-2,3,4,9-tetrahydroisothiazolo[5,4-b]quinoline-3,4-dione, 9-ethyl-6,8-difluoro-7-(3-ethylaminomethylcyclopentyl)-2,3,4,9-tetrahydroisothiazolo[5,4-b]quinoline-3,4-dione, 9-cyclopropyl-6,8-difluoro-7-(3-aminocyclopentyl)-2,3,4,9-tetrahydroisothiazolo[5,4-b]quinoline-3,4-dione, 9-cyclopropyl-6,8-difluoro-7-(4-aminocyclohexyl)-2,3,4,9-tetrahydroisothiazolo[5,4-b]quinoline-3,4-dione, 9-cyclopropyl-6,8-difluoro-7-(3-ethylaminomethylcyclopentyl)-2,3,4,9-tetrahydroisothiazolo[5,4-b]quinoline-3,4-dione, 9-p-fluorophenyl-6,8-difluoro-7-(3-aminocyclopentyl)-2,3,4,9-tetrahydroisothiazolo[5,4-b]quinoline-3,4-dione, 9-o,p-difluorophenyl-6,8-dihydro-7-(3-aminocyclopentyl)-2,3,4,9-tetrahydroisothiazolo[5,4-b]quinoline-3,4-dione.

Other preferred compounds of the invention having $R_2$ and R when taken together have the formula $-X-CH_2-CHR_6-$ wherein X is O oxygen are:

9-fluoro-10-(3-aminocyclopentyl)-3-methyl-7-oxo-2,3-dihydro-7H-pyrido-(1,2,3-de)-1,4-benzoxazine-6-carboxylic acid, 9-fluoro-10-(4-aminocyclohexyl)-3-methyl-7-oxo-2,3-dihydro-7H-pyrido-(1,2,3-de)-1,4-benzoxazine-6-carboxylic acid, 1-methyl-4-(3-aminocyclopentyl-5-fluoro-1,2,8,9-tetrahydro-7H-isoxazolo[4',5':5,6]-pyrido[1,2,3-de][1,4]benzoxazine-7,8-dione, 1-methyl-4-(4-aminocyclohexyl)-5-fluoro-1,2,8,9-tetrahydro-7H-isoxazolo[4',5':5,6-]pyrido[1,2,3-de][1,4]benzoxazine-7,8-dione, 1-methyl-4-(3-ethylaminomethylcyclopentyl)-5-fluoro-1,2,8,9-tetrahydro-7H-isoxazolo[4',5':5,6-]pyrido[1,2,3-de][1,4]benzoxazine-7,8-dione, 1-methyl-4-(3-aminocyclopentyl)-5-fluoro-1,2,8,9-tetrahydro-7H-isothiazolo[4',5':5,6]pyrido[1,2,3-de][1,4]benzoxazine-7,8-dione, 1-methyl-4-(4-aminocyclohexyl)-5-fluoro-1,2,8,9-tetrahydro-7H-isothiazolo[4',5':5,6-]pyrido[1,2,3-de][1,4]benzoxazine-7,8-dione, 1-methyl-4-(3-ethylaminomethylcyclopentyl)-5-fluoro-1,2,8,9-tetrahydro-7H-isothiazolo[4',5':5,6-]pyrido[1,2,3-de][1,4]benzoxazine-7,8-dione.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of formula I. The salts can be prepared in situ during the final isolation and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts, and the like. It has been found that the compounds of the present invention possess antibacterial activity against a wide spectrum of gram-positive and gram-negative bacteria, as well as enterobacteria. The compounds of the invention are therefore useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram-positive and gram-negative, aerobic and anaerobic organisms whose growth can be inhibited by the compounds of the invention such as Staphylococcus, Lactobacillus, Streptococcus, Sarcina, Escherichia, Enterbacter, Klebsiella, Pseudomonas, Acinetobacter, Proteus, Providencia, Citrobacter, Nisseria, Baccillus, Bacteroides, Campylobacter, Peptococcus, Clostridium, Salmonella, Shigella, Serratia, Legionella, Haemophilus, Brucella, and other organisms.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level, therefore, depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times per day.

The compounds of formula I (wherein A is N, $R_1$ is OH or alkoxy, $R_3$ is H and Z, R is as defined above) may be prepared by reactions shown in schemes A and B. In these schemes, L is a halogen, mesylate, tosylate or methoxy group, and $R_{10}$ is $C_1$–$C_4$ alkyl or benzyl, n is 1 or 2, and $R_7$ is as defined previously.

SCHEME A

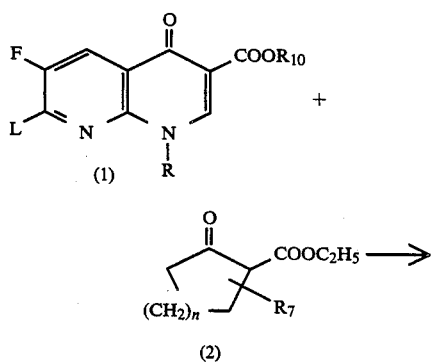

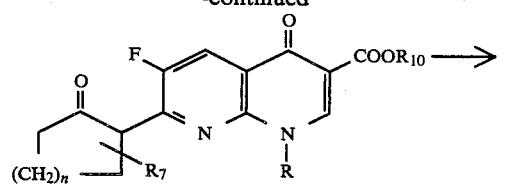

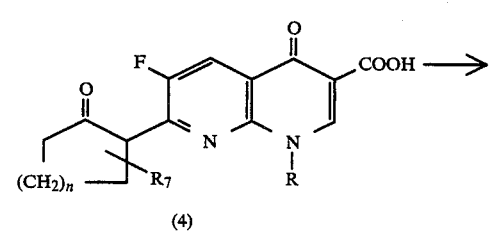

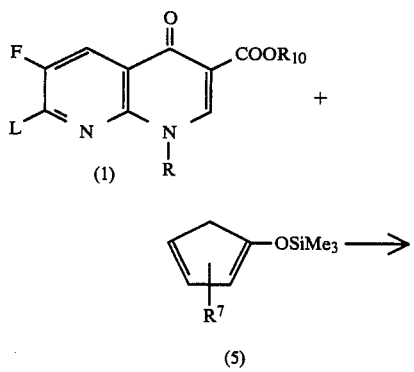

SCHEME B

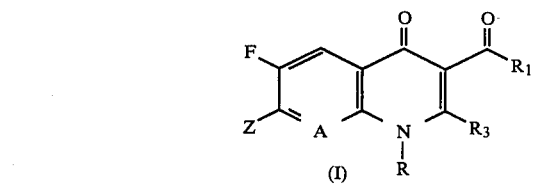

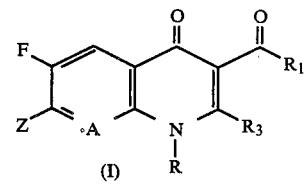

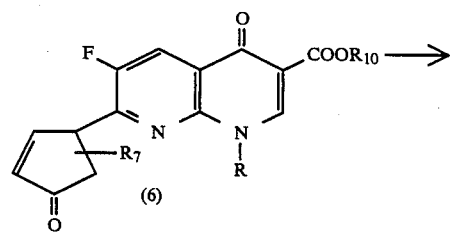

In accordance with the foregoing reaction schemes A and B, the naphthyridine (1) is reacted with the β-keto esters (2) in the presence of a base such as lithium disoproylamide (LDA) or sodium hydride or potassium t-butoxide in an organic solvent such as tetrahydrofuran (THF), dimethylformamide (DMF), t-butanol, dimethoxyethane (DME), and dimethylsulfoxide (DMSO) or chlorobenzene at a temperature from −40° to 120° C. to give the condensation product (3). Hydrolysis of (3) with 3N hydrochloric acid at 60° to 100° C. yields the corresponding acid which undergoes decarboxylation to yield compound (4). Reduction of the ketone function of compound (4) with a hydride reagent such as sodium borohydride in a suitable solvent such as methanol and acidic dehydration gives an olefin which is reduced by hydrogen gas in the presence of a catalyst such as Raney nickel to afford the deoxygenated product (I) A=N, $R_1$=OH, Z=

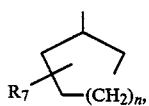

$R_3$=H). Alternately, compound (4) can be converted to its oxime upon treatment with hydroxylamine in methanol at room temperature. Subsequent hydrogenation in the presence of a suitable catalyst such as Raney nickel in an organic solvent such as methanol provides the amino-naphthyridine derivative (I) (A=N, $R_1$=OH, $R_3$=H, Z=

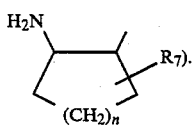

If Z is a five-membered carbocyclic ring, compound (I) wherein A=N can also be prepared in accordance with Scheme B. Reacting the naphthyridine (1) with a substituted cyclopentadiene (5) in the presence of a catalytic amount of zinc bromide at a temperature of −10° to 45° C. in an inert solvent (such as THF, methylene chloride or chloroform) yields the alpha, beta-unsaturated ketone derivative (6). This compound can then be converted into its oxime derivative upon treatment of (6) with hydroxylamine in methanol. Hydrogenation of the resulting oxime with Raney nickel in an organic solvent such as methanol yields the amino-naphthyridine derivative (I) (A=N, Z=

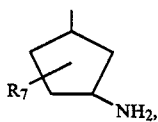

$R_3$=H).

The compounds of formula I (wherein A is $CR_2$, $R_1$ is hydroxy or alkoxy, $R_3$ is hydrogen, and Z, R and $R_2$ are as defined above) may be prepared by reactions shown in Scheme C. L is a halogen, mesylate, tosylate or methoxy group and $R_{10}$ is $C_1$-$C_4$ alkyl or benzyl, n is 1 or 2 and $R_7$ is as defined above.

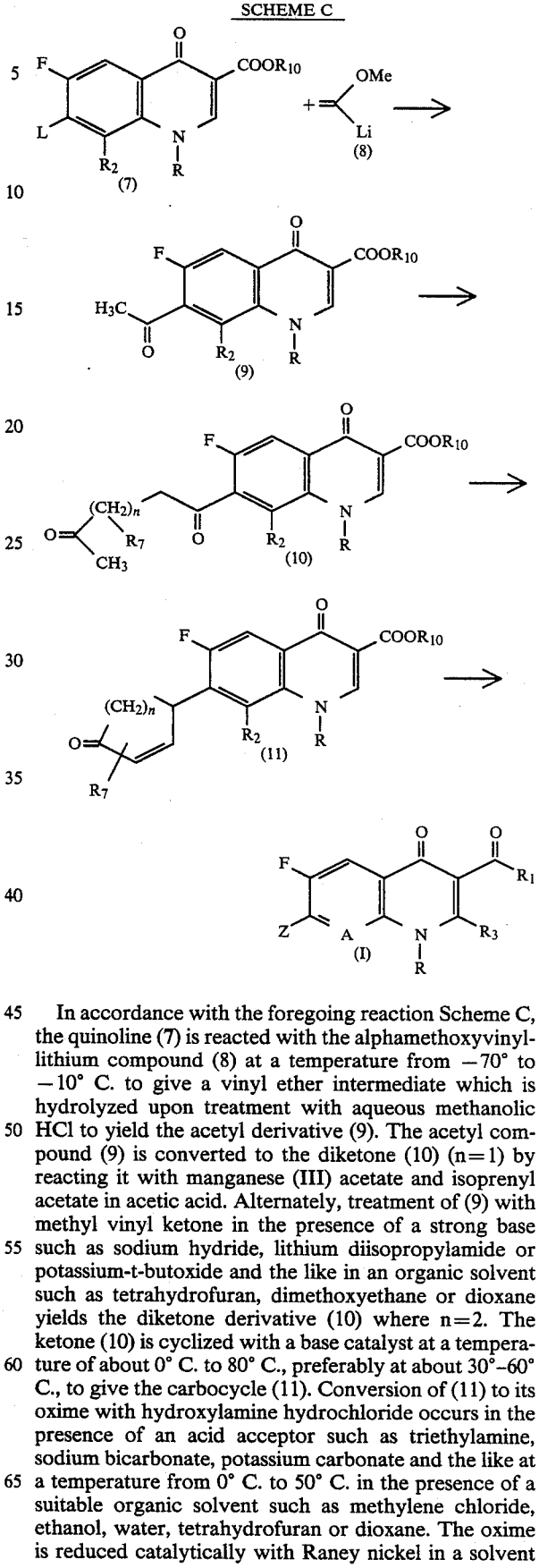

In accordance with the foregoing reaction Scheme C, the quinoline (7) is reacted with the alphamethoxyvinyllithium compound (8) at a temperature from −70° to −10° C. to give a vinyl ether intermediate which is hydrolyzed upon treatment with aqueous methanolic HCl to yield the acetyl derivative (9). The acetyl compound (9) is converted to the diketone (10) (n=1) by reacting it with manganese (III) acetate and isoprenyl acetate in acetic acid. Alternately, treatment of (9) with methyl vinyl ketone in the presence of a strong base such as sodium hydride, lithium diisopropylamide or potassium-t-butoxide and the like in an organic solvent such as tetrahydrofuran, dimethoxyethane or dioxane yields the diketone derivative (10) where n=2. The ketone (10) is cyclized with a base catalyst at a temperature of about 0° C. to 80° C., preferably at about 30°–60° C., to give the carbocycle (11). Conversion of (11) to its oxime with hydroxylamine hydrochloride occurs in the presence of an acid acceptor such as triethylamine, sodium bicarbonate, potassium carbonate and the like at a temperature from 0° C. to 50° C. in the presence of a suitable organic solvent such as methylene chloride, ethanol, water, tetrahydrofuran or dioxane. The oxime is reduced catalytically with Raney nickel in a solvent such as methanol, tetrahydrofuran or hexane to give the quinoline or naphthyridine derivative (I) (Z=

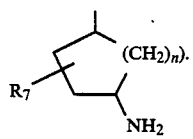

Alternatively, catalytic reduction of compound (11) with palladium, platinum or platinum oxide in the presence of an hydrogen atmosphere yields the keto intermediate. This compound is treated with nitromethane and a base such as potassium-t-butoxide or sodium methoxide and the like in an aprotic such as THF, dichloromethane, dioxane or DMF at temperature of about 0° C., to about 60° C., followed by treating the resultant product with Raney nickel in the presence of an aldehyde to yield (I)

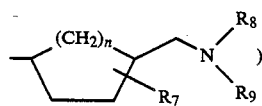

wherein $R_8$ and $R_9$ are as defined previously.

If $R_1$ in (I) is not hydroxy, the ester is subjected to hydrolysis such as by treatment with aqueous sodium hydroxide or mineral acid to form the free carboxylic acid ($R_1$=OH).

If desired, the 1,4-dihydro-4-oxo-1,8-naphthyridine- (or quinoline)3-carboxylic acid (I, A=N or $CR_2$, $R_1$=H) can be converted into a corresponding ester by conventional esterification procedures, such as by treating the free acid (I, $R_1$=OH) with the appropriate alcohol in the presence of an acid catalyst by converting the free acid (I, $R_1$=OH) into the corresponding acid chloride followed by displacement of the chloro radical with the appropriate alcohol, or by treating the sodium salt of the acid with a suitable reactive halide, such as chloromethylpivalate in dimethoxyethane to obtain, for example, the pivaloyloxymethyl ester I ($R_1$=—OCH$_2$OCOC(CH$_3$)$_3$).

The compounds of formula I (wherein $R_3$ and $R_1$ taken together in Y—NH where Y is oxygen or sulfur and A, R and Z are as defined above) may be prepared by reactions shown in Scheme D. L is a halogen, mesylate, tosylate or methoxy group and $R_{10}$ is $C_1$-$C_4$ alkyl or benzyl, n is 1 or 2, $R_7$ and $R_8$ and $R_9$ are as defined above, and $R_{11}$ is $C_1$-$C_4$ alkyl or phenyl and substituted phenyl.

SCHEME D

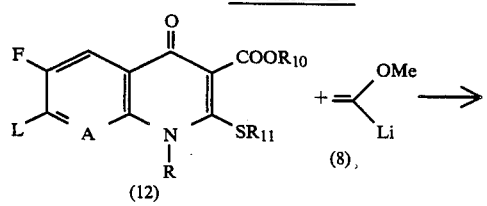

-continued
SCHEME D

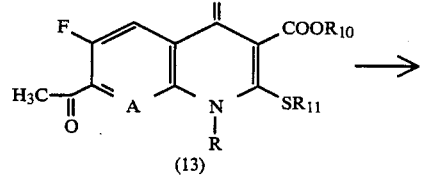

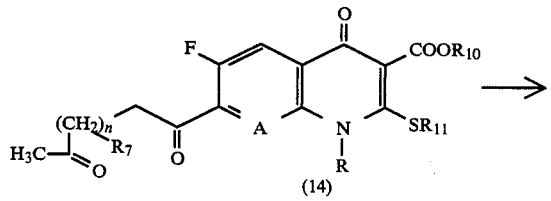

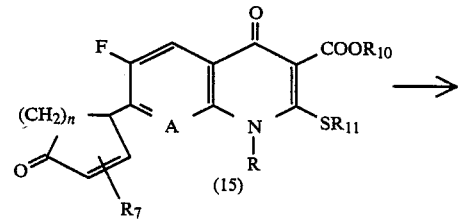

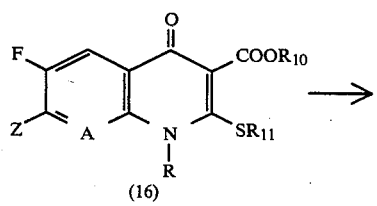

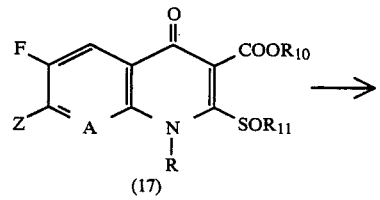

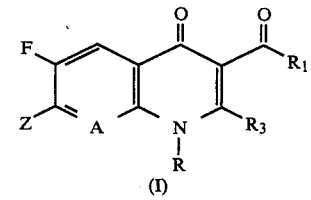

In accordance with the foregoing reaction Scheme D, quinoline (12) is reacted with the alphamethoxyvinyllithium (8) at a temperature from −70° to −10° C. to give a vinyl ether intermediate which is hydrolysed upon treatment with aqueous methanolic HCl to yield the acetyl derivative (13). The acetyl compound (13) is converted to the diketone (14) (n=1) upon reaction with maganese (III) acetate and isoprenyl acetate in acetic acid. Alternatively, treatment of (14) with methyl vinyl ketone in the presence of a strong base such as sodium hydride, lithium diisopropylamide or potassium-t-butoxide and the like in an organic solvent (such as tetrahydrofuran, dimethoxyethane or dioxane) yields the diketone derivative (14) were n=2. The diketone (14) is cyclized with a base catalyst at a temperature of about 0° to 80° C., preferably at about 30° to 60° C., to give the carbocyclic derivative (15). Conversion of (15) to its oxime with hydroxylamine hydrochloride occurs in the presence of an acid acceptor such as triethylamine, sodium bicarbonate, potassium carbonate and the like at a temperature from 0° C. to 50° C. in the presence of a suitable organic solvent (such as methylene chloride, ethanol, water, tetrahydrofuran or dioxane). The oxime is reduced catalytically with pallidium on charcoal in a solvent such as methanol, ethanol, tetrahydrofuran or hexane to give the quinoline or naphthyridine derivative (16) Z=

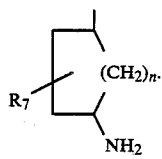

Alternately, catalytic reduction of compound (15) with palladium, platinum or platinum oxide in hydrogen atmosphere yields the keto intermediate. This is treated with nitromethane and a base such as potassium-t-butoxide or sodium methoxide and the like in an aprotic solvent such as THF, dichloromethane, dioxane or DMF, at temperature of about 0° C. to about 60° C., followd by catalytic hydrogenation of the product with palladium on chrcoal. Reductive alkylation with sodium cyanoborohydride yields the compound (16) (Z=

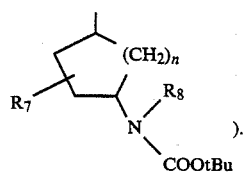

The free primary or secondary amine of compound (16) is then protected by a t-butoxycarbonyl group upon treatment with di-t-butyl dicarbonate in the presence of a base such as triethylamine to yield compound (16) (Z=

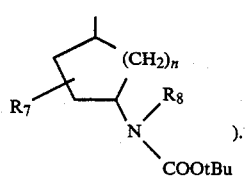

Oxidation of compound (16) with meta-chloroperbenzoic acid or another peroxy acid yields the sulfoxide (17). The reaction may be conducted at a temperature from 0° C. to 50° C. in the presence of a solvent.

Reaction of (17) with sodium hydrosulfide in an appropriate solvent, preferably aqueous tetrahydrofuran, at low or elevated temperature yields the 2-mercaptoderivative (16). ($R_{11}$=H). Treatment of this product with hydroxylamine-O-sulfonic acid in the presence of a base, preferably sodium bicarbonate in an organic solvent, (preferably aqueous tetrahydrofuran) yields the isothiazolo derivatives (I). ($R_3, R_1$=S—NH).

Alternatively, treatment of the sulfoxide (17) with hydroxyurea in an organic solvent or a mixture of organic solvents such as tetrahydrofuran and methanol in the presence of a base such as 1,8-diazabicyclo[5.4.0]undec-7-ene (DBU) or 1,5-diazabicyclo[4.3.0]non-5-ene (DBN) at room temperature or suitable elevated temperature as desired yields the isoxazolo derivative (I) ($R_3, R_1$=O—NH).

If the Z group has a t-butoxycarbonyl protecting group, this group is removed by treatment with trifluoroacetic acid to give (I) wherein Z is

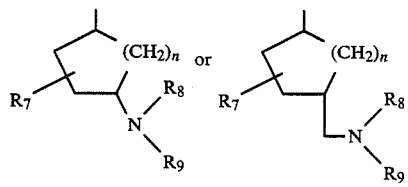

Methods for preparing the starting materials described in Schemes A, B C (e.g., compounds (1) and (7)) are analogous to those described in the art; Chu et al., J. Med. Chem., 28, 1558 (1985); Chu et al., J. Med. Chem., 29, 2363 (1986); Chu, J. Heterocyclic Chem., 22, 1033 (1985); Wentland et al., J. Med. Chem., 27, 1103 (1984), HiRai et al., Abs. #436, 26th Intersci, Conf. Antimicrob. Agents and Chemother., 1986; Matsumoto et. al., Chem. Pharm. Bull., 34, 4098 (1986) and Albrecht, Prog. Drug Research 21, 9 (1977) and references cited therein.

A method for preparing compound (12) used in Scheme D is described in Scheme E wherein q is a halogen.

SCHEME E

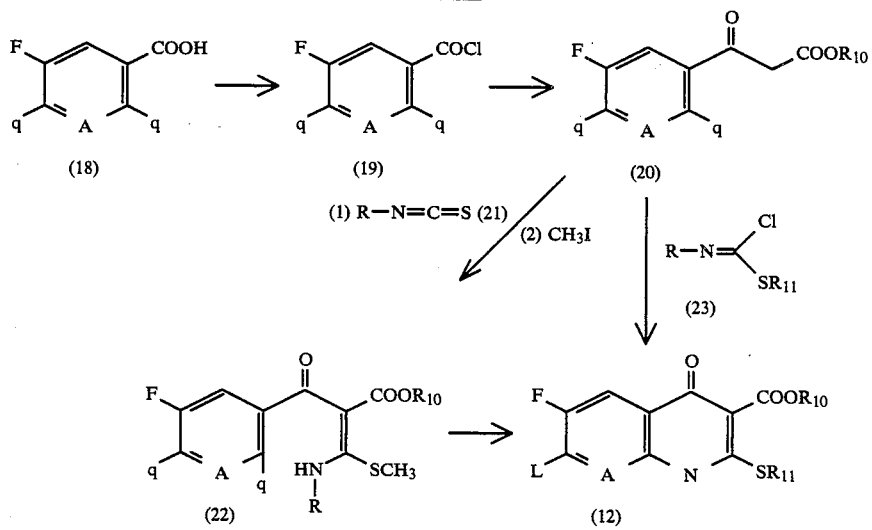

In accordance with the foregoing reaction scheme, the substituted benzoic acid of nicotinic acid (18) can be converted to its acid chloride (19) by treatment with thionyl chloride. Displacement of the acid chloride (19) with malonic acid half ester in the presence of n-butyllithium yields the beta-ketoester (20). Treatment of the beta-ketoester (20) with sodium hydride in an aprotic solvent, (preferably tetrahydrofuran) with substituted isothiocyanate (21) at 0° to 40° C. for 3-36 hours followed by the addition of methyl iodide yields the enaminoketoester (22). The latter reaction may be conducted at room temperature or at a suitable elevated temperature, as desired.

The enaminoketoester (22) is then cyclized, such as by treatment with a strong base, preferably sodium hydride, to obtain the 1,4-dihydro-4-oxo-quinoline-3-carboxylic acid ester (12) (A=CR$_2$) or 1,4-dihydro-4-oxo-1,8-naphthyridine-3-carboxylic acid ester (12) (A=N). Cyclization is conducted in the presence of an aprotic solvent, such as dimethoxyethane, bis(2-methoxyethyl)ether, dimethylformamide, tetrahydrofuran or chlorobenzene, and is preferably conducted at temperatures of about 20° C. to about 145° C., more preferably at the reflux temperature of the solvent employed.

Alternatively, the 3-carboxylic acid ester (12) can be prepared by treatment of the beta-ketoester (20) with sodium hydride in an aprotic solvent, (preferably tetrahydrofuran or toluene) and reaction with alkyl or phenyl N-substituted iminochlorothioformate (23) at room temperature or at a suitable elevated temperature as desired.

The compounds of the formula (9) may be prepared in accordance with the following reaction Scheme F, in which X is N, CF, CH, or CCl.

SCHEME F

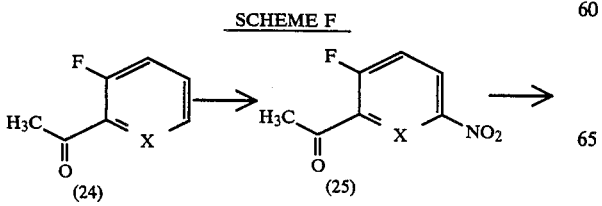

-continued
SCHEME F

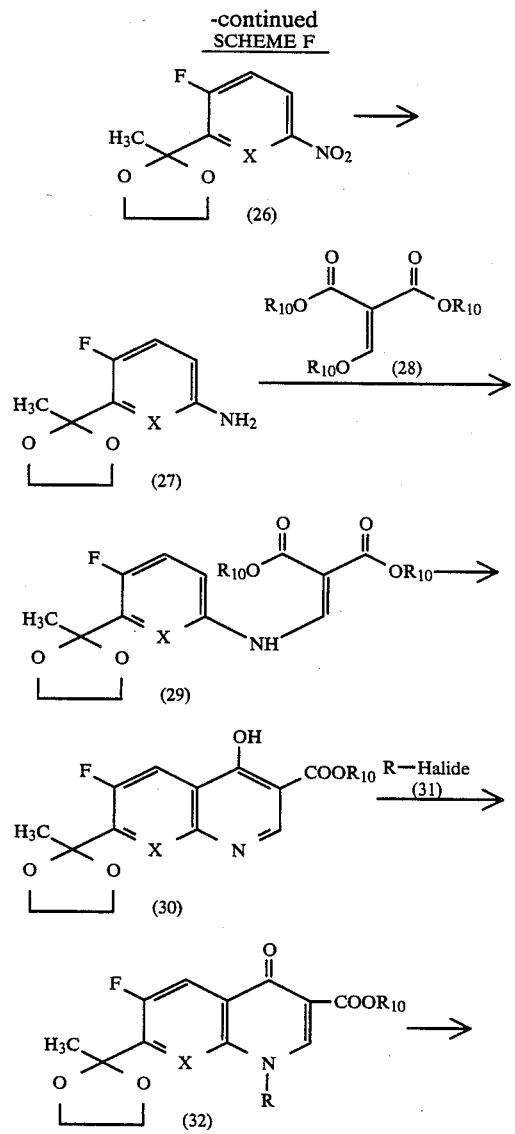

-continued
SCHEME F

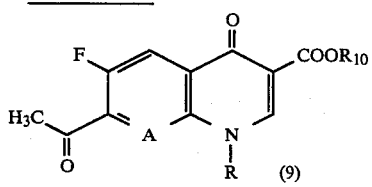

In accordance with the foregoing reaction scheme, the known fluoroacetophenone (24) is nitrated with nitric acid to give the nitrofluoroacetophenone (25). The ketone (25) is converted to a ketal (26) by reaction with a 1,2-glycol, preferably ethylene glycol in the presence of an acid catalyst, (preferably p-toluenesulfonic acid) in an aprotic organic solvent such as methylcyclohexane, benzene or toluene at a temperature from about 50° C. to about 150° C., preferably at the reflux temperature of the solvent employed. Reduction of (26) in the presence of hydrogen and a catalyst, (e.g., Raney nickel) in a protic organic solvent such a methanol, ethanol or isopropanol yields the amine (27). Reaction of the amine (27) with the appropriate alkoxymethylenemalonate ester (28) in a protic or aprotic organic solvent (such as toluene, tetrahydrofuran, dimethylformamide, or methylcyclohexane) or preferably using (28) as the solvent at a temperature of about 80° C. to about 150° C., (preferably at about 120° C.) yields the enaminoketoester (29), which may be isolated or carried on without isolation. Cyclization of the latter in an aprotic organic solvent (preferably diphenyl ether) at temperatures of about 200° C. to about 300° C., (preferably at about 240° C. to 260° C.) leads to (30). The latter may be alkylated with an appropriate alkyl or aromatic halide (31), where the halide is as described above. The alkylation is conducted in the presence of a base catalyst (e.g., triethylamine, sodium ethoxide or sodium hydroxide, preferably potassium carbonate) in the presence of an aprotic organic solvent (e.g., dimethoxyethane, tetrahydrofuran, 1,2-dichloroethane, chlorobenzene, or dimethylformamide) at a temperature of about 25° C. to about 125° C. (more preferably at temperatures of about 50° to about 70° C.) to form (32). Removal of the ketal protecting group from (32) in the presence of a mineral acid or an organic acid catalyst leads to the ester of formula (9).

Alternatively, the compound of formula (9) may be prepared in accordance with the following reaction Scheme G, in which X is N, CF, CH or CCl.

SCHEME G

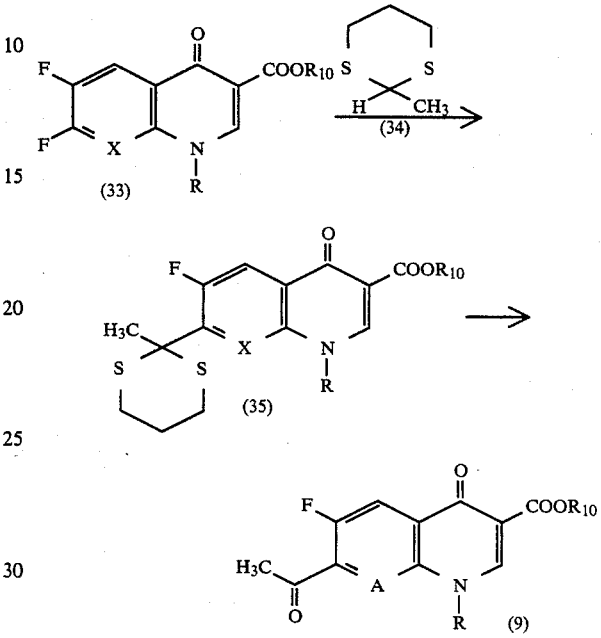

In accordance with the foregoing reaction scheme, the ester (33) is reacted with the anion of (34), which is generated by reaction of (34) with a strong base (e.g., butyllithium, lithium diisopropylamine and the like) in an aprotic solvent such as dimethoxyethane, diethyl ether or more preferably tetrahydrofuran, to lead to the dithiane derivatives (35). The dithiane protecting group is removed from (35) by reaction with methyl iodide in a suitable organic solvent such as methanol, ethanol or acetonitrile at temperatures of about 20° C. to about 100° C., (preferably at the reflux temperature of the solvent employed), yielding the ester of formula (9).

A method for preparing compound (12) wherein $R_2$ and R taken together is —O—CH$_2$—CH(R$_6$)— is described by Scheme H wherein q is a halogen.

SCHEME H

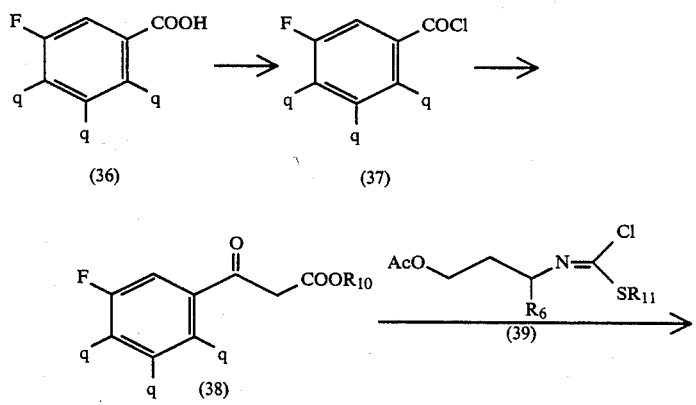

-continued
SCHEME H

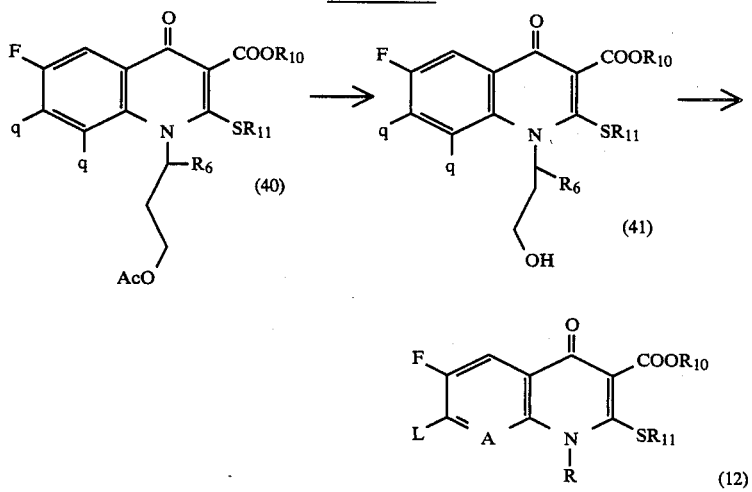

In accordance with the foregoing reaction scheme (H), the substituted benzoic acid (36) can be converted to its acid chloride (37) by treatment with thionyl chloride. Displacement of the acid chloride (37) with malonic acid half ester in the presence of n-butyllithium yields the beta-ketoester (38).

The alkyl 2-(2,3,4-trihalo-5-fluoro) benzoylacetate (38) can be converted to the 1,4-dihydro-4-oxo-quinoline-3-carboxylic acid ester (40) by treatment of (38) with sodium hydride in an aprotic solvent, preferably THF or toluene, and then reacting the resulting enolate with N-substituted iminochlorothioformate (39) at room temperature or at an elevated temperature as desired. Treatment of the ester (40) with dilute acid in aqueous acetonitrile or other suitable solvent for a period of time gives the alcohol (41). Reaction of this alcohol (41) in an aprotic solvent such as THF with sodium hydride or a strong base such as sodium hydroxide or lithium dialkylamides (e.g., lithium diisopropylamide or lithium bistrimethylsilylamide) yields the 9-fluoro-10-halo-3-alkyl-5-substituted thio-7-oxo-2,3-dihydro-7-pyrido[1,2,3-de][1,4]benzoxazine-6-carboxylic acid ester (12).

The foregoing reaction schemes may be better understood from the following examples, which are presented for purposes of illustration and are not intended to limit the scope of the inventive concepts. As used in the following examples, the references to compounds, such as (1), (2), (3), etc. and to substituents such as R, $R_1$, X, A, etc., refer to the corresponding compounds and substituents in the foregoing reaction schemes and in formula I.

EXAMPLE 1

1-p-Fluorophenyl-6-fluoro-1,4-dihydro-4-oxo-7-(2-aminocyclohexyl)-1,8-naphthyridine-3-carboxylic acid (a) To a solution of 6.8 grams of 2-carboethoxycyclohexanone (2) ($R_7$=H, n=2) in 20 ml of tetrahydrofuran (THF) is added 2.9 grams of 50% NaH mineral oil dispersion (ice bath). To the resulting suspension is added 3.65 grams of (1) (L=Cl, R=p-fluorophenyl, $R_{10}$=$C_2H_5$). The reaction mixture is heated at reflux for one day and partitioned between saturated aqueous $NaHCO_3$ and chloroform. The chloroform solution is dried and concentrated. The crude product is purified by silica gel column chromatography to yield (3) ($R_7$=H, n=2, R=p-fluorophenyl, $R_{10}$=$C_2H_5$).

(b) To a solution of 2.6 grams of (3) from above in 50 ml of THF is added 100 ml of 6M aqueous HCl. The reaction mixture is heated at 90° C. for four hours and concentrated to obtain the decarboxylated material compound (4) ($R_7$=H, n=2, R=p-fluorophenyl $R_{10}$=H). The crude material is used in subsequent transformations without further purification.

(c) To a stirring solution of 0.35 grams of $H_2NOH$ HCl in 5 ml of $H_2O$ is added 0.42 grams of solid $NaHCO_3$. After gas evolution ceases, a mixture of 2.1 grams of compound 4($R_7$=H, n=2, R=P-fluorophenyl,) in 5 ml of $CH_3OH$ is added to the system. After stirring at room temperature for one day, the reaction mixture is concentrated. The crude oxime is collected and recrystallized from ethanol. The oxime (2.2 g) is suspended in 50 ml of ethanol, and 2.0 grams of Raney nickel is added to the system. The system is placed under an atmosphere of $H_2$. After 24 hours, the catalyst is removed by filtration and the filtrate is concentrated. The residue may be recrystallized from ethanol to obtain 1-p-fluorophenyl-6-fluoro-1,4-dihydro-4-oxo-7-(1-aminocyclohexyl)-1,8-naphthyridine-3-carboxylic acid (I) (Z=

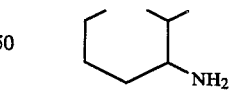

R=p-fluorophenyl, $R_3$=H, $R_1$=OH, A=N).

EXAMPLE 2

1-Cyclopropyl-6-fluoro-1,4-dihydro-4-oxo-7-(3-aminocyclopentyl)-1,8-naphthyridine-3-carboxylic acid (a) 3.1 grams of compound (5) ($R_7$=H) are mixed with 5 ml of THF and placed under a nitrogen atmosphere. While stirring the solution at −78° C., 4.5 grams of $ZnBr_2$ is added, followed by 3.1 grams of compound (1) (L=Cl, R=cyclopropyl, $R_{10}$=$C_2H_5$). The reaction mixture is then allowed to come to room temperature. After one day, the mixture is partitioned between $CHCl_3$ and saturated aqueous $NaHCO_3$. The $CHCl_3$ layer is washed with brine, dried (with $Na_2SO_4$) and concentrated. The residue is subjected to column chromatography to obtain the condensation product (6) ($R_7$=H, R=cyclopropyl, $R_{10}$=$C_2H_5$).

(b) To a stirring solution of 0.35 gram of $H_2NOH'HCl$ in 5 ml of water is added 0.42 grams of solid $NaHCO_3$. A solution of 1.8 grams of (6) prepared from above in methyl alcohol is added to the system. After stirring for one day, the reaction mixture is concentrated. The crude material is recrystallized from ethanol. The purified oxime (1.5 grams) is placed in 40 ml of ethanol. Two grams of Raney nickel is added, and the system is placed under a hydrogen atmosphere. After one day, the catalyst is removed by filtration, and the filtrate is concentrated. The residue is dissolved in 2.5 ml of THF. While stirring this solution, 50 ml of 0.1M aqueous NaOH is added. The reaction mixture is heated at about 65° C. for four hours and concentrated. The resulting solid is slurried in 1M aqueous HCl and collected by suction filtration. The solid is rinsed with 1M aqueous HCl, ethanol, and ether. The solid is dissolved in water, and this solution is brought to pH=7 with saturated aqueous $NaHCO_3$. The resulting free base 1-cyclopropyl-6-fluoro-1,4-dihydro-4-oxo-7-(3-aminocyclopentyl)-1,8-naphthyridine-3-carboxylic acid (I) is collected by suction filtration and dried in a vacuum oven. (Z=

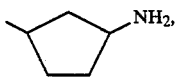

A=N, R=cyclopropyl, $R_3$=H, $R_1$=OH). Alternatively, the condensation between (4) and (5) (Example 2a) may be catalyzed by other Lewis acids such as $ZnCl_2$ or $TiCl_4$ or sources of fluoride ion such as KF or $nBu_4NF$. The same product may also be obtained by condensation of the dienolate derived from cyclopentenone and a strong base such as LDA with compound (1).

EXAMPLE 3

1-p-Fluorophenyl-6-fluoro-1,4-dihydro-4-oxo-7-(3-aminocyclopentyl)-1,8-naphthyridine-3-carboxylic acid The procedure of Example 2 can be repeated replacing compound (1) in Example 2(a) with compound 1(L=Cl, R=p-fluorophenyl, $R_{10}$=$C_2H_5$) to obtain 1-p-fluorophenyl-6-fluoro-1,4-dihydro-4-oxo-7-(3-aminocyclopentyl)-1,8-naphthyridine-3-carboxylic acid (I). (Z=

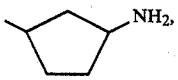

A=N, R=p-fluorophenyl, $R_3$=H, $R_1$=OH).

EXAMPLE 4

1-o,p-Difluorophenyl-6-fluoro-1,4-dihydro-4-oxo-7-(3-aminocyclopentyl)-1,8-naphthyridine-3-carboxylic acid The procedure of Example 2 can be repeated replacing compound (1) in Example 2(a) with compound (1) (L=Cl, R=2,4-difluorophenyl, $R_{10}$=$C_2H_5$) to obtain 1-o,p-difluorophenyl-6-fluoro-1,4-dihydro-4-oxo-7-(3-aminocyclopentyl)-1,8-naphthyridine-3-carboxylic acid (I) (Z=

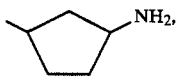

A=N, R=2,4-difluorophenyl, $R_3$=H, $R_1$=OH).

EXAMPLE 5

1-Cyclopropyl-6-fluoro-1,4-dihydro-4-oxo-7-(4-aminocyclohexyl)-1,8-naphthyridine-3-carboxylic acid The procedure of Example 2 can be repeated replacing compound 5 in Example 2a with

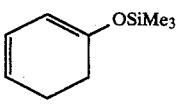

to obtain 1-cyclopropyl-6-fluoro-1,4-dihydro-4-oxo-7-(4-aminocyclohexyl)-1,8-naphthyridine-3-carboxylic acid (I) (Z=

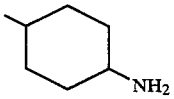

R=cyclopropyl, A=N, $R_3$=H, $R_1$=OH).

EXAMPLE 6

1-Cyclopropyl-6-fluoro-1,4-dihydro-4-oxo-7-(3-phenyliminocyclopentyl)-1,8-naphthyridine-3-carboxylic acid In a round-bottomed flask equipped with a magnetic stirring bar are placed 2 grams of (I) the product of Example 2 (Z=

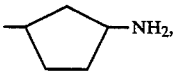

A=N, R=cyclopropyl, $R_3$=H, $R_1$=OH), 20 ml of toluene, and 1.5 ml of benzaldehyde. The system is equipped with a Dean-Stark trap containing four angstrom molecular sieves. The reaction mixture is heated at reflux for one day and cooled to room temperature. The solid imine (I) Z=

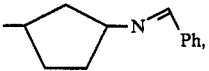

A=N, R=cyclopropyl, $R_3$=H, $R_1$=OH) is collected by suction filtration.

EXAMPLE 7

1-Cyclopropyl-6-fluoro-1,4-dihydro-4-oxo-7-(3-p-fluorophenyliminocyclopentyl)-1,8-naphthyridine-3-carboxylic acid The procedure described in Example 6 can be repeated replacing the benzaldehyde with p-fluorobenzaldehyde to obtain 1-cyclopropyl-6-fluoro-1,4-dihydro-4-oxo-7-(3-p-fluorophenyliminocyclopentyl)-1,8-naphthyridine-3-carboxylic acid (I) (Z=

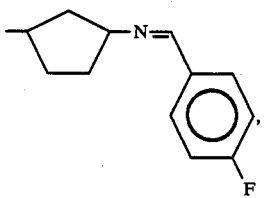

A=N, R=cyclopropyl, $R_3$=H, $R_1$=OH).

EXAMPLE 8

1-p-Fluorophenyl-6-fluoro-1,4-dihydro-4-oxo-7-(3-phenyliminocyclopentyl)-1,8-naphthyridine-3-carboxylic acid The procedure described in Example 6 can be repeated replacing compound (I) of Example (2) with the product (I) of Example (3) to obtain 1-(p-fluorophenyl)-6-fluoro-1,4-dihydro-4-oxo-7-(3-phenyliminocyclopentyl)-1,8-naphthyridine-3-carboxylic acid (I). (Z=

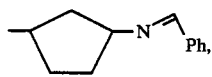

A=N, R=p-fluorophenyl, $R_3$=H, $R_1$=OH).

EXAMPLE 9

1-Cyclopropyl-6-fluoro-1,4-dihydro-4-oxo-7-(4-phenyliminocyclohexyl)-1,8-naphthyridine-3-carboxylic acid The procedure of Example 6 can be repeated replacing compound (I), product of Example (2) with compound (I), product of Example (5) to obtain 1-cyclopropyl-6-fluoro-1,4-dihydro-4-oxo-7-(4-phenyliminocyclohexyl)-1,8-naphthyridine-3-carboxylic acid (I) (Z=

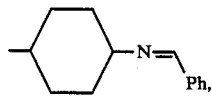

A=N, R=cyclopropyl, $R_3$=H, $R_1$=OH).

EXAMPLE 10

1-p-Fluorophenyl-6-fluoro-1,4-dihydro-4-oxo-7-(3-ethylaminomethylcyclopentyl)-1,8-naphthyridine-3-carboxylic acid (a) Following the procedure described in Examples 1(a) and (b) and replacing 2-carboethoxycyclohexanone (2) with 2-carboethoxy-4-ethylaminomethylcyclopentan-1-one (2) ($R_7$=$C_2H_5$—NHCH$_2$—, n=1), one can obtain 1-p-fluorophenyl-6-fluoro-1,4-dihydro-4-oxo-7-(5-keto-3-ethylaminomethylcyclopentyl)-1,8-naphthyridine-3-carboxylic acid (I) (Z=

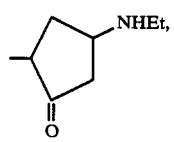

A=N, $R_3$=H, $R_1$=OH, R=p-fluorophenyl).

(b) Two grams of (I) from Example 10(a) is dissolved in 50 ml of methanol saturated with anhydrous hydrogen chloride. After standing at room temperature for one day, the solvent is removed yielding the hydrochloride salt of (I) (Z=

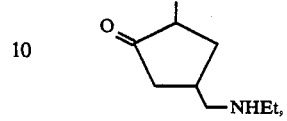

A=N, $R_3$=H, $R_1$=OCH$_3$, R=p-fluorophenyl.

(c) 0.1 gram of sodium borohydride is added to a solution of one gram of compound (I) from Example 10(b) in 50 ml of ethanol. After six hours, acetic acid (0.2 ml) is added, and the solvent is evaporated to dryness. The residue is partitioned between methylene chloride and water. The organic layer is dried and evaporated to dryness. The crude product is then dissolved in 5 ml pyridine and 2 ml of acetic anhydride. It is heated at 90° C. for one day. The solvent is then removed yielding (I) (Z=

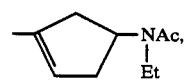

A=N, $R_3$=H, $R_1$=OCH$_3$, R=p-fluorophenyl).

(d) One gm of (I) from Example 3(c) is dissolved in 10 ml of acetic acid and is hydrogenated under hydrogen atmosphere using 0.5 gram of palladium on charcoal as catalyst. After one day, the reaction mixture is filtered, and the filtrate is evaporated to dryness. The crude product is suspended in 30 ml of 4N hydrochloric acid and heated at 80° C. for six hours. The solvent is removed, and the product is crystallized from dimethylsulfoxide to yield the title compound (I) (Z=

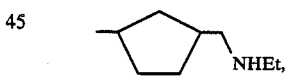

A=N, $R_3$=H, $R_1$=OH, R=p-fluorophenyl).

EXAMPLE 11

1-Cyclopropyl-6-fluoro1,4-dihydro-4-oxo-7-(3-ethylaminomethylcyclopentyl)-1,8-naphthyridine-3-carboxylic acid Example 10 can be repeated, replacing the compound (1) (L=Cl, R=p-fluorophenyl, $R_{10}$=$C_2H_5$) with compound (1) (L=Cl, R=cyclopropyl, $R_{10}$=$C_2H_5$). One can obtain 1-cyloporopyl-6-fluoro-1,4-dihydro-4-oxo-7-(3-ethylaminomethylcyclopentyl)-1,8-naphthyridine-3-carboxylic acid (I) (Z=

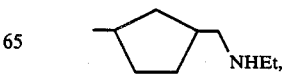

A=N, $R_3$=H, $R_1$=OH, R=cyclopropyl).

EXAMPLE 12

1-Ethyl-6-fluoro-1,4-dihydro-4-oxo-7-(3-ethylaminomethylcyclopentyl)-1,8-naphthyridine-3-carboxylic acid Following the procedure of Example 10, replacing the compound (1) (L=Cl, R=p-fluorophenyl, $R_{10}=C_2H_5$) with compound (1) (L=Cl, R=ethyl, $R_{10}=C_2H_5$) one can obtain 1-ethyl-6-fluoro-1,4-dihydro-4-oxo-7-(3-ethylaminomethylcyclopentyl)-1,8-naphthyridine-3-carboxylic acid (I) (Z=

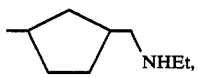

A=N, $R_3$=H, $R_1$=OH, R=$C_2H_5$).

EXAMPLE 13

1-Cyclopropyl-6-fluoro-1,4-dihydro-4-oxo-7-(2-aminocyclohexyl)-1,8-naphthyridine-3-carboxylic acid Example 1 can be repeated replacing the compound (1) (L=Cl, R=p-fluorophenyl, $R_{10}=C_2H_5$) with compound (1) (L=Cl, R=cyclopropyl, $R_{10}=C_2H_5$) to obtain 1-cyclopropyl-6-fluoro-1,4-dihydro-4-oxo-7-(2-aminocyclohexyl)-1,8-naphthyridine-3-carboxylic acid (I) (Z=

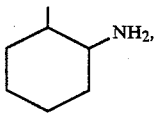

R=cyclopropyl, $R_3$=H, $R_1$=OH, A=N).

EXAMPLE 14

1-Ethyl-6-fluoro-1,4-dihydro-4-oxo-7-(3-aminocyclopentyl)-1,8-naphthyridine-3-carboxylic acid The procedure of Example 2 can be repeated, replacing compound (1), in Example 2(a) with compound (1) (L=Cl, R=$C_2H_5$, $R_{10}=C_2H_5$) to obtain 1-ethyl-6-fluoro-1,4-dihydro-4-oxo-7-(3-aminocyclopentyl)-1,8-naphthyridine-3-carboxylic acid (I) (Z=

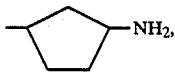

A=N, $R_3$=H, $R_1$=OH, R=$C_2H_5$).

EXAMPLE 15

1-Ethyl-6-fluoro-1,4-dihydro-4-oxo-7-(4-aminocyclohexyl)-1,8-naphthyridine-3-carboxylic acid The procedure of Example 5 can be repeated, replacing the compound (1) (L=Cl, R=cyclopropyl, $R_{10}=C_2H_5$) with the compound (1) (L=Cl, R=$C_2H_5$, $R_{10}=C_2H_5$) to obtain 1-ethyl-6-fluoro-1,4-dihydro-4-oxo-7-(4-aminocyclohexyl)-1,8-naphthyridine-3-carboxylic acid (I) (Z=

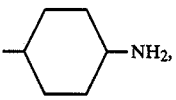

$R_3$=H, A=N, $R_1$=OH, R=$_2H_5$)

EXAMPLE 16

1-Ethyl-6-fluoro-1,4-dihydro-4-oxo-7-(4-aminocyclohexyl)quinoline-3-carboxylic acid (a) A solution of 167 grams 2-fluoroacetophenone (24) (X=CH) is added to 680 ml of concentrated $H_2SO_4$ at $-20°$ C. Then a mixture of 96 ml fuming $HNO_3$ and 284 ml of concentrated $H_2SO_4$ is added over a period of several hours. This mixture is poured into 7500 ml ice, the resulting solid is dissolved in ether and is washed with 5% aqueous $NaHCO_3$ and $H_2O$. After drying, 173 grams of a pale yellow solid (25) (X=CH) is obtained (mp, 51°-55° C.). To this compound (25) (55 grams) in 500 ml of benzene is added 17 ml of ethylene glycol and 0.57 grams of p-toluenesulfonic acid. The reaction mixture is heated under reflux for 20 hours with azeotropic removal of water. The reaction mixture is washed with 5% aqueoua $NaHCO_3$ and $H_2O$ and dried to yield 64.7 grams of a yellow oil (26) (X=CH).

(b) A solution of the 64.7 grams of the ketal (26) (X=CH) in 1 L of methanol, is reduced under hydrogen atmosphere with 6.5 grams of Raney nickel. The reaction mixture is filtered, and the solvent is removed under reduced pressure. The residue is dissolved in 1 L of $CH_2Cl_2$ and is filtered through florisil, which is washed with an additional 1 L of $CH_2Cl_2$. The combined solutions are evaporated to dryness yielding 46.4 g of a tan solid (27) (X=CH) mp 76°-78° C.

A suspension of 25 grams of the amine (27) (X=CH) in 27.8 ml of diethylethoxymethyenemalonate (28) ($R_1$=R-ethyl) is heated at 120° C. for three hours. Ethanol is removed under reduced pressure. The crude product (29) (X=CH, $R_{10}$=ethyl) is used without purification. The enaminoester (29) is dissolved in 200 ml of diphenylether. The solution is added dropwise over a period of two hours to 600 ml of diphenylether heated at 255° C. while stirring. The solution is maintained at 255° C. for one hour after the addition is complete. After cooling to room temperature, the solution is diluted with 2 L of hexane. The resulting precipitate is isolated by suction filtration and is washed with acetone, yielding 10.2 grams of a tan solid (30) (X=CH, $R_{10}$=ethyl), m.p. 259°-260° C.

(c) To a solution of 8.4 grams of (30) (X=CH, $R_{10}$=ethyl) in 90 ml of dimethylformamide is added 7.2 grams of $K_2CO_3$. The reaction mixture is heated at 75° C. for 30 minutes. Then, 6.4 ml of (31) (R=$C_2H_5$, HALIDE=I) ethyliodide is added, and the reaction mixture is heated at 75° C. for 20 hours. The dimethylformamide is removed under reduced pressure. The residue is dissolved in 300 ml of $CH_2Cl_2$, and is washed with water and dried.

The solvent is removed under reduced pressure, and the residue is recrystallized from $CH_2Cl_2$, yielding 9.0 grams of (32) (X=C, $R_{10}$=R=ethyl) as a white solid, mp, 122°-124° C. A solution of 7.2 grams of (32) (X=CH, $R_{10}$=R=ethyl) in 30 ml of trifluoroacetic acid and 60 ml of 2N CHl is heated at 75° C. for eight hours. The trifluoroacetic acid is then removed under reduced pressure. The resulting precipitate is isolated y suction filtration. The precipitate is recrystallized from isopropanol/chloroform yielding 4.8 grams of a white solid (9) (A=CH, R=ethyl, $R_{10}$=H), m.p. 247°–249° C.

This acid can be converted to the ester as follows:

To a suspension of 3.5 grams of (9) (A=CH, R=ethyl, $R_{10}$=H) in 40 ml of acetonitrile is added 2.9 ml of 1,8-diazbicyclo[5.4.0]undec-7-ene and 2.7 ml of ethyliodide. The reaction mixture is stirred at room temperature for 22 hours. The reaction mixture is diluted with 250 ml of $CH_2Cl_2$ and is washed with 1N CHl, 10% $Na_2CO_3$ and $H_2O$. After drying, the solvent is removed under reduced pressure, and the residue is recrystallized from $CH_2Cl_2$, yielding 3.1 grams of (9) as a white solid (A=CH, $R_{10}$=R=ethyl), m.p. 122°–124° C.

(d) A solution of 3.0 grams of (9) (A=CH, $R_{10}$=R=ethyl) in 35 ml dimethylformamide and 3.2 ml of chlorotrimethylsilane and 8.7 ml of triethylamine is heated at 130° C. for 36 hours. The solvent is removed under reduced pressure. The residue is dissolved in $CH_2Cl_2$ and is washed with water. After drying, the solvent is removed under reduced pressure. The residue is dissolved in 30 ml of $CH_2Cl_2$ and is cooled to −70° C. Methyl vinyl ketone, (0.77 grams) and 10 ml of 1.0M titanium tetrachloride in $CH_2Cl_2$ are added. After one hour at −70° C., the reaction mixture is poured into 150 grams of ice and is extracted with $CH_2Cl_2$. After drying, the solvent is removed under reduced pressure, and the residue is recrystallized from $CH_2Cl_2$ giving 2.0 grams of (10) (A=CH, $R_{10}$=R=ethyl, $R_7$=H, n=2).

(e) A solution of 1.5 grams of (10) from part 16(d) and 0.15 grams of potassium tert-butoxide in 15 ml of ethanol is heated at 60° C. for 18 hours. The solution is then diluted with 200 ml water and extracted with $CH_2Cl_2$. After drying, the solvent is removed under reduced pressure yielding 1.0 grams of (11) (A=CH, $R_{10}$=R=ethyl, $R_7$=H, n=2). The ketone (11) (1.0 gram) is converted to its oxime derivative by reaction with 750 mg of hydroxylamine hydrochloride and 850 mg of sodium bicarbonate in 30 ml of 1:1 ethanol/water at room temperature for 18 hours. The ethanol is then removed under reduced pressure. The resulting precipitate is isolated by suction filtration, yielding 820 mg of a white solid which is dissolved in 100 ml of methanol and is reduced with hydrogen and 800 mg of Raney nickel at room temperature for 18 hours. After filtration, the solvent is removed under reduced pressure, yielding 760 mg of a yellow solid (I) (A=CH, R=$C_2H_5$, $R_1$=$OC_2H_5$, Z=

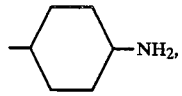

$R_3$=H).

(f) To a suspension of 500 mg of compound (I) from part 16(e) above in 7 ml of tetrahydrofuran is added 0.54 ml of 1N NaOH. The reaction mixture is heated at 65° C. for 1.5 hours. The pH is adjusted to 4 with 1N CHl, and the solution is evaporated to dryness. The residue is suspended in 200 ml of 1:1 ethanol/$CH_2Cl_2$ and is filtered. The solvent is removed under reduced pressure to yield 200 mg of the hydrochloride salt of compound (I) (A=CH, R=$C_2H_5$, $R_1$=OH, $R_5$=H, Z=

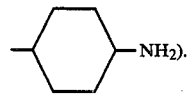

EXAMPLE 17

1-Ethyl-6,8-difluoro-1,4-dihydro-4-oxo-7-(4-aminocyclohexyl)-quinoline-3-carboxylic acid The procedure of Example 16 can be repeated replacing 2-fluoroacetophenone in Example 16(a) with 2,6-difluoroacetophenone to obtain 1-ethyl-6,8-difluoro-1,4-dihydro-4-oxo-7-(4-aminocyclohexyl)-quinoline-3-carboxylic acid (I) (A=CF, R=$C_2H_5$, $R_1$=OH, $R_3$=H, Z=

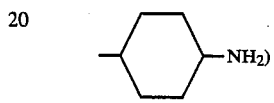

and its hydrochloride salt.

EXAMPLE 18

1-Ethyl-6-fluoro-8-chloro-1,4-dihydro-4-oxo-7-(4-aminocyclohexyl)quinoline-3-carboxylic acid (a) The procedure of Example 16 can be repeated, replacing 2-fluoroacetophenone in Example 16(a) with 2-chloro-6-fluoroacetophenone to obtain 1-ethyl-6-fluoro-8-chloro-1,4-dihydro-4-oxo-7-(4-aminocyclohexyl)-quinoline-3-carboxylic acid (I) (A=CCl, R=$C_2H_5$, $R_1$=OH, $R_3$=H, Z=

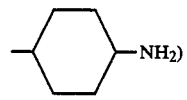

and its hydrochloride salt.

EXAMPLE 19

1-Cyclopropyl-6-fluoro-1,4-dihydro-4-oxo-7-(4-aminocyclohexyl)quinoline-3-carboxylic acid (a) A solution of 5.0 grams of 1-cyclopropyl-6,7-difluoro-1,4-dihydro-4-oxo-quinoline-3-carboxylic acid ethyl ester (33) (X=CH, $R_{10}$=ethyl, R=cyclopropyl) in 50 ml of tetrahydrofuran is added a solution of the anion of (34), prepared by reaction of 2.4 grams of 2-methyl-1,3-dithiane with 7.5 ml of 2.5N n-butyllithium at −78° C. in 50 ml of tetrahydrofuran. The reaction mixture is stirred at −78° C. for four hours. The reaction is quenched by pouring the mixture into water. The mixture is extracted with $CH_2Cl_2$. After drying, the solvent is removed under reduced pressure to give 5.2 grams of (35) Z=CH, $R_{10}$=ethyl, r=cyclopropyl) as a yellow solid. A solution of 5.2 grams of (35) (X=CH, $R_{10}$=ethyl, R=cyclopropyl) in 30 ml of acetonitrile is treated with 1.1 ml of methyliodide for 24 hours. The reaction mixure is diluted with 150 ml of water and is extracted with $CH_2Cl_2$. After drying, the solvent is removed under reduced pressure to give 3.5 grams of (9) (A=CH, $R_{10}$=ethyl, R=cyclopropyl) as a white solid.

(b) By following the example 16(d), (e) and (f) replacing 1-ethyl-6-fluoro-7-acetyl-1,4-dihydro-4-oxo-quinoline-3-carboxylic acid ethyl ester (9) (A=CH, $R_{10}$=R=ethyl) with 1-cyclopropyl-6-fluoro-7-acetyl-1,4-dihydro-4-oxo-quinoline-3-carboxylic acid ethyl ester (9) (A=CH, $R_{10}$=ethyl, R=cyclopropyl), one can obtain 1-cyclopropyl-6-fluoro-1,4-dihydro-4-oxo-7-(4-aminocyclohexyl)quinoline-3-carboxylic acid (I) (A=CH, R=cyclopropyl, $R_1$=OH, $R_3$=H, Z=

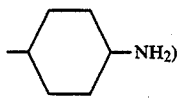

and its hydrochloride salt.

EXAMPLE 20

1-o,p-Difluorophenyl-6-fluoro-1,4-dihydro-4-oxo-7-(4-aminocyclohexyl)quinoline-3-carboxylic acid In the described fashion as Example 19 replacing 1-cyclopropyl-6,7-difluoro-1,4-dihydro-4-oxo-quinoline-3-carboxylic acid ester (33) (X=CH, $R_{10}$=ethyl, R=cyclopropyl) with 1-o,p-difluorophenyl-6,7-difluoro-1,4-dihydro-4-oxo-quinoline-3-carboxylic acid ethyl ester (33) (X=CH, $R_{10}$=ethyl, R=o,p-difluorophenyl), one can obtain 1-o,p-difluorophenyl-6-fluoro-1,4-dihydro-4-oxo-7-(4-aminocyclohexyl)-quinoline-3-carboxylic acid (I) (A=CH, $R_1$=OH, $R_3$=H, R=o,p-difluorophenyl, Z=

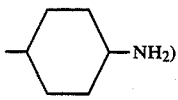

and its hydrochloride salt.

EXAMPLE 21

1-Ethyl-6-fluoro-1,4-dihydro-4-oxo-7-(3-aminocyclopentyl)quinoline-3-carboxylic acid (a) The procedure of Example 16 can be repeated for Example (16(a), (b) and (c) yielding 1-ethyl-6-fluoro-7-acetyl-1,4-dihydro-4-oxo-quinoline-3-carboxylic acid ethyl ester (9) (A=CH, $R_{10}$=R=ethyl).

(b) A solution of 3 grams of compound (9) from Example 21(a) (A=CH, $R_{10}$=R=ethyl) in 25 ml of glacial acetic acid is mixed with 8 grams of manganese (III) acetate dihydrate and 3.7 ml of isoprenyl acetate. The mixture is heated at 70° C. for three hours. The reaction mixture is poured into water and is extracted with $CH_2Cl_2$. After drying, the solution is evaporated to dryness and is purified through a silica gel column yielding 1.5 grams of a yellow oil. A solution of 1.5 grams of this yellow oil 0.19 gram of potassium tert-butoxide in 30 ml of ethanol is heated at 60° C. for 18 hours. The reaction mixture is diluted with 100 ml water and is extracted with $CH_2Cl_2$. After drying, the solvent is removed under reduced pressure yielding 1.1 gram of (11) (A=CH, $R_7$=H, n=1, $R_{10}$=R=ethyl).

(c) A solution of 1.1 gram of compound (11) ofExample 21(b) (A=CH, $R_7$=H, n=1, $R_{10}$=R=ethyl) in 30 ml of 1:1 ethanol/water is reacted with 900 mg of hydroxylamine hydrochloride and 950 mg of sodium bicarbonate at room temperature for 24 hours. The ethanol is removed under reduced pressure. The resulting precipitate is isolated by suction filtration yielding 900 mg of the oxime. The oxime is dissolved in 100 ml of methanol, and is reduced with 900 mg of Raney nickel under a hydrogen atmosphere at room temperature for 18 hours. After filtration, the solvent is removed under reduced pressure yielding 800 mg of a yellow solid (I) (A=CH, R=$C_2H_5$, $R_3$=H, $R_1$=$OC_2H_5$, Z=

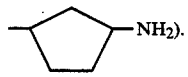

(d) The procedure of Example 16(f) can be repeated replacing 1-ethyl-6-fluoro-1,4-dihydro-4-oxo-7-(4-aminocyclohexyl)-quinoline-3-carboxylic acid ethyl ester (I) with 1-ethyl-6-fluoro-1,4-dihydro-4-oxo-7-(3-aminocyclopentyl)quinoline-3-carboxylic acid ethyl ester (I) product of Example 21(c) to obtain 1-ethyl-6-fluoro-1,4-dihydro-4-oxo-7-(3-aminocyclopentyl)quinoline-3-carboxylic acid (I) (A=CH, R=$C_2H_5$, $R_3$=H, $R_1$=OH, Z=

and its hydrochloride salt.

EXAMPLE 22

1-Cyclopropyl-6-fluoro-1,4-dihydro-4-oxo-7-(3-aminocyclopentyl)quinoline-3-carboxylic acid (a) The procedure of Example 19(a) can be repeated to obtain 1-cyclopropyl-6-fluoro-7-acetyl-1,4-dihydro-4-oxo-quinoline-3-carboxylic acid ethyl ester (9) (A=CH, $R_{10}$=ethyl, R=cyclopropyl).

(b) In the described fashion as Example 21(b), (c), and (d) replacing 1-ethyl-6-fluoro-7-acetyl-1,4-dihydro-4-oxo-quinoline-3-carboxylic acid ethyl ester (9) (A=CH, $R_{10}$=R=ethyl) with 1-cyclopropyl-6-fluoro-7-acetyl-1,4-dihydro-4-oxo-quinoline-3-carboxylic acid ethyl ester (9) (A=CH, $R_{10}$=ethyl, R=cyclopropyl) one can obtain 1-cyclopropyl-6-fluoro-1,4-dihydro-4-oxo-7-(3-aminocyclopentyl)quinoline-3-carboxylic acid (I) (A=CH, $R_3$=H, $R_1$=OH, Z=

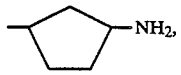

R=cyclopropyl) and its hydrochloride salt.

EXAMPLE 23

1-p-Fluorophenyl-6-fluoro-1,4-dihydro-4-oxo-7-(3-aminocyclopentyl)quinoline-3-carboxylic acid (a) The procedure of Example 19(a) can be repeated with 1-(p-fluorophenyl)-6,7-difluoro-1,4-dihydro-4-oxo-quinoline-3-carboxylic acid ethyl ester (33) (X=CH, $R_{10}$=ethyl, R=p-fluorophenyl) replacing 1-cyclopropyl-6,7-difluoro-1,4-dihydro-4-oxo-quinoline-3-carboxylic acid ethyl ester (33) (X=CH, $R_{10}$=ethyl, R=cyclopropyl) to obtain 1-p-fluorophenyl-6-fluoro-7-acetyl-1,4-dihydro-4-oxo-quinoline-3-carboxylic acid (9) (A=CH, $R_{10}$=ethyl, R=p-fluorophenyl).

(b) In the described fashion as Example 21(b), (c), and (d) replacing 1-ethyl-6-fluoro-7-acetyl-1,4-dihydro-4- oxo-quinoline-3-carboxylic acid ethyl ester (9) (A=CH, R$_{10}$=R=ethyl) with 1-p-fluorophenyl-6-fluoro-7-acetyl-1,4-dihydro-4-oxo-quinoline-3-carboxylic acid ethyl ester (9) (A=CH, R$_{10}$=ethyl, R=p-fluorophenyl) one can obtain 1-p-fluorophenyl-6-fluoro-1,4-dihydro-4-oxo-7-(3-aminocyclopentyl)quinoline-3-carboxylic acid (I) (A=CH, R$_1$=OH, R$_3$=H, R=p-fluorophenyl, Z=

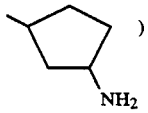

and its hydrochloride salt.

EXAMPLE 24

1-Ethyl-6-fluoro-1,4-dihydro-4-oxo-7-(3-aminomethyl-1-cyclopentyl)-quinoline-3-carboxylic acid (a) The procedure for Example 16(a), (b) and (c) can be repeated yielding 1-ethyl-6-fluoro-7-acetyl-1,4-dihydro-4-oxo-quinoline-3-carboxylic acid ethyl ester (9) (A=CH, R$_{10}$=R=ethyl).

(b) The procedure of Example 21(b) can be repeated to obtain 1-ethyl-6-fluoro-1,4-dihydro-4-oxo-7-(3-cyclopentyl-2-enone)quinoline-3-carboxylic acid ethyl ester (11) (A=CH, R$_7$=H, n=1, R$_{10}$=R=ethyl). The ketone (11) (3 grams) in 30 ml of dimethylformamide is mixed with 1.6 ml of nitromethane. The mixture is treated with 0.11 gram of potassium tert-butoxide. After stirring at room temperature overnight, the reaction mixture is diluted with water and extracted with CH$_2$Cl$_2$. After drying, the solvent is removed under reduced pressure. The 3 grams of product in 25 ml of dimethyl sulfoxide is treated with acetic anhydride at room temperature for 24 hours. After removal of the DMSO under reduced pressure, the residue is diluted with water and is extracted with CH$_2$Cl$_2$. After drying, the solvent is removed under reduced pressure. The product is dissolved in ethanol and is reduced with sodium borohydride. The reaction mixture is acidified with 1N HCl and is extracted with CH$_2$Cl$_2$. After drying, the solvent is removed under reduced pressure. The product is dissolved in ethanol and reduced with Raney nickel under a hydrogen atmosphere at room temperature. After removing the catalyst by filtration, the solvent is removed under reduced pressure giving a yellow solid which is recrystallized from ethanol to give an off-white solid (I) (A=CH, R$_3$=H, R=C$_2$H$_5$, R$_1$=OC$_2$H$_5$, Z=

(c) The procedure of Example 16(f) can be repeated, replacing 1-ethyl-6-fluoro-1,4-dihydro-4-oxo-7-(4-aminocyclohexyl)quinoline-3-carboxylic acid ethyl ester (I) (A=CH, R$_3$=H, R=C$_2$H$_5$, R$_1$=OC$_2$H$_5$, Z=

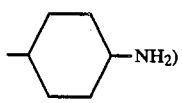

with 1-ethyl-6-fluoro-1,4-dihydro-4-oxo-7-(3-aminomethyl-1-cyclopentyl)-quinoline-3-carboxylic acid ethyl ester (I) from Example 24(b), to obtain 1-ethyl-6-fluoro-1,4-dihydro-4-oxo-7-(3-aminomethyl-1-cyclopentyl)-quinoline-3-carboxylic acid (I) (A=CH, R$_3$=H, R=C$_2$H$_5$, R$_1$=OH, Z=

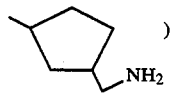

and its hydrochloride salt.

EXAMPLE 25

1-Ethyl-6-fluoro-1,4-dihydro-4-oxo-7-(3-ethylaminomethyl-1-cyclopentyl)-quinoline-3-carboxylic acid (a) In the described fashion as Example 24(a), (b) and (c), one can obtain 1-ethyl-6-fluoro-1,4-dihydro-4-oxo-7-(3-aminomethyl-1-cyclopentyl)quinoline-3-carboxylic acid (I) (A=CH, R$_3$=H, R=C$_2$H$_5$, R$_1$=OH, Z=

(b) The preceding compound (I) in methanol is reduced with palladium on carbon in the presence of acetaldehyde at room temperature for 18 hours. The catalyst is removed by filtration, and the solvent is removed under reduced pressure giving a yellow solid which is recrystallized from methanol to give 1-ethyl-6-fluoro-1,4-dihydro-4-oxo-7-(3-ethylaminomethyl-1-cyclopentyl)-quinoline-3-carboxylic acid (I) (A=CH, R$_3$=H, R=C$_2$H$_5$, R$_1$=OH, Z=

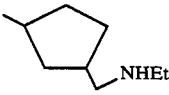

and its hydrochloride salt.

EXAMPLE 26

1-Cyclopropyl-6-fluoro-1,4-dihydro-4-oxo-7-(3-ethylaminomethyl-1-cyclopentyl)quinoline-3-carboxylic acid (a) The procedure of Example 19(a) can be repeated to obtain 1-cyclopropyl-6-fluoro-7-acetyl-1,4-dihydro-4-oxo-quinoline-3-carboxylic acid ethyl ester (9) (A=CH, R$_{10}$=ethyl, R=cyclopropyl).

(b) In the described fashion as Example 24(b) and (c), replacing 1-ethyl-6-fluoro-7-acetyl-1,4-dihydro-4-oxo-quinoline-3-carboxylic acid ethyl ester (9) (A=CH, R$_{10}$=R=ethyl) with 1-cyclopropyl-6-fluoro-7-acetyl-1,4-dihydro-4-oxo-quinoline-3-carboxylic acid ethyl ester (9) (A=CH, R$_{10}$=ethyl, R=cyclopropyl), one can obtain 1-cyclopropyl-6-fluoro-1,4-dihydro-4-oxo-7-(3-aminomethyl-1-cyclopentyl)-quinoline-3-carboxylic acid (I) (A=CH, R$_3$=H, R=cyclopropyl, R$_1$=OH, Z=

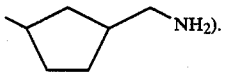

(c) In the described fashion as Example 25(b), -(3-aminomethyl-1-cyclopentyl)-quinoline-3-carboxylic acid (I) (A=CH, R₃=H, R=C₂H₅, R₁=OH, Z=

with 1-cyclopropyl-6-fluoro-1,4-dihydro-4-oxo-7-(3-aminomethyl-1-cyclopentyl)quinoline-3-carboxylic acid (I) (A=CH, R₃=H, R=cyclopropyl R₁=OH, Z=

one can obtain 1-cyclopropyl-6-fluoro-1,4-dihydro-4-oxo-7-(3-ethylaminomethyl)-1-cyclopentyl)-quinoline-3-carboxylic acid (I) (A=CH, R₃=H, R=cyclopropyl, R₁=OH, Z=

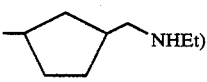

and its hydrochloride salt.

EXAMPLE 27

1-Cyclopropyl-6-fluoro-1,4-dihydro-4-oxo-7-(3-propylaminomethyl-1-cyclopentyl)-quinline-3-carboxylic acid In the described fashion of Example 26, replacing acetaldehyde with propionaldehyde in Example 26(c), one can obtain 1-cyclopropyl-6-fluoro-1,4-dihydro-4-oxo-7-(3-propylaminomethyl-1-cyclopentyl)-quinoline-3-carboxylic acid (I) (A=CH, R₃=H, R=cyclopropyl, R₁=OH, Z=

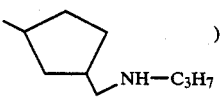

and its hydrochloride salt.

EXAMPLE 28

1-p-Fluorophenyl-6-fluoro-1,4-dihydro-4-oxo-7-(3-methylaminomethyl-1-cyclopentyl)-quinoline-3-carboxylic acid (a) In the described fashion as Example 23(a), one can obtain 1-p-fluorophenyl-6-fluoro-7-acetyl-1,4-dihydro-4-oxo-quinoline-3-carboxylic acid ethyl ester (9) (A=CH, R₁₀=ethyl, R=p-fluorophenyl).

(b) In the described fashion of Example 24(b), replacing 1-ethyl-6-fluoro-7-acetyl-1,4-dihydro-4-oxo-quinoline-3-carboxylic acid ethyl ester with 1-p-fluorophenyl-6-fluoro-7-acetyl-1,4-dihydro-4-oxo-quinoline-3-carboxylic acid ethyl ester (9) (A=CH, R₁₀=ethyl, R=p-fluorophenyl), one can obtain 1-p-fluorophenyl-6-fluoro-1,4-dihydro-4-oxo-7-(3-aminomethyl-1-cyclopentyl)-quinoline-3-carboxylic acid (I) (A=CH, R₃=H, R=p-fluorophenyl, R₁=OH, Z=

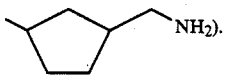

(c) The preceding compound (I) following Example 25(b) with and replacing acetaldehyde with formaldehyde, one can obtain 1-p-fluorophenyl-6-fluoro-1,4-dihydro-4-oxo-7-(3-methylaminomethyl-1-cyclopentyl)-quinoline-3-carboxylic acid (I) (A=CH, R₃=H, R=p-fluorophenyl, R₁=OH, Z=

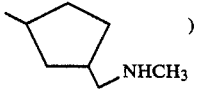

and its hydrochloride salt.

EXAMPLE 29

1-Ethyl-6-fluoro-1,4-dihydro-4-oxo-7-(1-aminoethyl)-quinoline-3-carboxylic acid (a) In the described fashion as Example 16(a), (b) and (c), one can obtain 1-ethyl-6-fluoro-7-acetyl-1,4-dihydro-4-oxo-quinoline-3-carboxylic acid ethyl ester (9) (A=CH, R₁₀=R=ethyl).

(b) In the described fashion as Example 21(c) and 21(d) replacing the 1-ethyl-6-fluoro-1,4-dihydro-7-(3-cyclopent-2-enone)quinoline-3-carboxylic acid ethyl ester with the preceding compound (9), one can obtain 1-ethyl-6-fluoro-1,4-dihydro-4-oxo-7-(1-aminoethyl)-quinoline-3-carboxylic acid (I) (A=CH, R=C₂H₅, R₁=OH, Z=CH(NH₂)CH₃) and its hydrochloride salt.

EXAMPLE 30

1-Ethyl-6-fluoro-1,4-dihydro-4-oxo-7-(1-ethylaminoethyl)quinoline-3-carboxylic acid (a) In the described fashion as Example 29, one can obtain 1-ethyl-6-fluoro-1,4-dihydro-4-oxo-7-(1-aminoethyl)-quinoline-3-carboxylic acid (I).

(b) In the described fashion as Example 26(c), using the preceding compound (I), one can obtain 1-ethyl-6-fluoro-1,4-dihydro-4-oxo-7-(1-ethylaminoethyl)quinoline-3-carboxylic acid (I) (A=CH, R=C₂H₅, R₃=H, R₁=OH, Z=CH—(NHC₂H₅)—CH₃) and its hydrochloride salt.

EXAMPLE 31

1-Cyclopropyl-6-fluoro-1,4-dihydro-4-oxo-7-(1-ethylaminoethyl)quinoline-3-carboxylic acid (a) In the described fashion as Example 19(a), one can obtain 1-cyclopropyl-6-fluoro-7-acetyl-1,4-dihydro-4-oxo-quinoline-3-carboxylic acid ethyl ester (9).

(b) In the described fashion as Example 26(b) and (c) replacing 1-ethyl-6-fluoro-7-acetyl-1,4-dihydro-4-oxo-quinoline-3-carboxylic acid ethyl ester (9) with the preceding compound (9) from 31(a), one can obtain 1-cyclopropyl-6-fluoro-1,4-dihydro-4-oxo-7-(1-(ethylaminoethyl)quinoline-3-carboxylic acid (I) (A=CH, R-cyclopropyl, R₃=H, R₁=OH, Z=—CH—(NHC₂H₅)CH₃) and its hydrochloride salt.

EXAMPLE 32

1-Ethyl-6-fluoro-1,4-dihydro-4-oxo-7-(3-ethylamino-1-cyclopentyl)quinoline-3-carboxylic acid The procedures of Example 21 can be repeated to obtain 1-ethyl-6-fluoro-1,4-dihydro-4-oxo-7-[3-aminocyclopentyl]-quinoline-3-carboxylic acid. In the described fashion of Example 26(c), replacing 1-ethyl-6-fluoro-1,4-dihydro-4-oxo-7-[3-(aminomethyl)-1-cyclopentyl]quinoline-3-carboxylic acid (I) with 1-ethyl-6-fluoro-1,4-dihydro-4-oxo-7-(3-aminocyclopentyl)quinoline-3-carboxylic acid (I) (A=CH, $R_3$=H, $R_1$=OH, R=$C_2H_5$, Z=

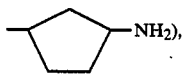

one can obtain 1-ethyl-6-fluoro-1,4-dihydro-4-oxo-7-(3-ethylaminocyclopentyl)quinoline-3-carboxylic acid (I) (A=CH, $R_3$=H, $R_1$=OH, R=$C_2H_5$, Z=

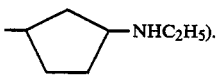

EXAMPLE 33

1-Cyclopropyl-6-fluoro-1,4-dihydro-4-oxo-7-(3-ethylaminocyclopentyl)quinoline-3-carboxylic acid The procedure of Example 22 can be repeated to obtain 1-cyclopropyl-6-fluoro-1,4-dihydro-4-oxo-7-(3-aminocyclopentyl)quinoline-3-carboxylic acid (I) (A=CH, $R_3$=H, $R_1$=OH, R=cyclopropyl, Z=

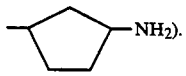

In the described fashion of Example 26(c), replacing 1-ethyl-6-fluoro-1,4-dihydro-4-oxo-7-(3-aminomethyl-1-cyclopentyl)quinoline-3-carboxylic acid (I) with the preceding described compound (I) (A=CH, $R_3$=H, $R_1$=OH, R=cyclopropyl, Z=

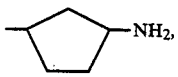

one can obtain 1-cyclopropyl-6-fluoro-1,4-dihydro-4-oxo-7-(3-ethylaminocyclopentyl)quinoline-3-carboxylic acid (I) (A=CH, $R_3$=H, $R_1$=OH, R=cyclopropyl, Z=

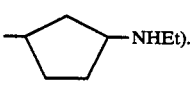

EXAMPLE 34

1-Cyclopropyl-6-fluoro-1,4-dihydro-4-oxo-7-(4-ethylaminocyclohexyl)quinoline-3-carboxylic acid The procedure of Example 19 can be repeated to obtain 1-cyclopropyl-6-fluoro-1,4-dihydro-4-oxo-7-(4-aminocyclohexyl)quinoline-3-carboxylic acid (I). In the described fashion as Example 26(c), replacing 1-ethyl-6-fluoro-1,4-dihydro-4-oxo-7-(3-aminomethyl-1-cyclopentyl)quinoline-3-carboxylic acid (I) with the preceding described compound (I) (A=CH, $R_3$=H, R=cyclopropyl, $R_1$=OH, Z=

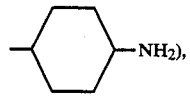

one can obtain 1-cyclopropyl-6-fluoro-1,4-dihydro-4-oxo-7-(4-ethylaminocyclohexyl)quinoline-3-carboxylic acid (I) (A=CH, $R_3$=H, R=cyclopropyl, $R_1$=OH, Z=

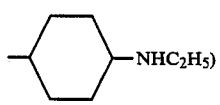

and its hydrochloride salt.

EXAMPLE 35

1-o,p-Difluorophenyl-6-fluoro-1,4-dihydro-4-oxo-7-(4-methylaminocyclohexyl)quinoline-3-carboxylic acid The procedure of Example 20 can be repeated to obtain 1-o,p-difluorophenyl-6-fluoro-1,4-dihydro-4-oxo-7-(4-aminocyclohexyl)quinoline-3-carboxylic acid (I). In the described fashion as Example 16(c), replacing 1-ethyl-6-fluoro-1,4-dihydro-4-oxo-7-(3-aminomethyl-1-cyclopentyl)quinoline-3-carboxylic acid (I) with the preceding compound (I) (A=CH, $R_3$=H, R=o,p-difluorophenyl, $R_1$=OH, Z=

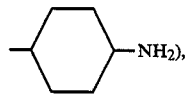

and replacing acetaldehyde with formaldehyde, one can obtain 1-o,p-difluorophenyl-6-fluoro-1,4-dihydro-4-oxo-7-(4-methylaminocyclohexyl)quinoline-3-carboxylic acid (I) (A=CH, $R_3$=H, R=o,p-difluorophenyl, $R_1$=OH, Z=

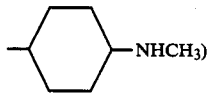

and its hydrochloride salt.

EXAMPLE 36

Ethyl-1-p-fluorophenyl-6,7-difluoro-2-methylthio-1,4-dihydro-4-oxo-quinoline-3-carboxylate (a) A mixture of 0.5 gram of 2,4,5-trifluorobenzoic acid (18) (A=CH, q=F) and thionyl chloride (4 ml) is heated at reflux for one hour. The solution is evaporated to dryness to give the acid chloride (19). This acid chloride is added to a solution of 2.50 grams of ethyl malonate monoester in 20 ml of tetrahydrofuran (THF) containing 0.51 gram of n-butyllithium at −65° C. The solution is allowed to warm to room temperature and is acidified and extracted with ether. The ether extract is washed with saturated aqueous NaHCO$_3$ and water, dried and concentrated to yield 0.59 gram of the ketoester (20) (A=CH, q=F, R$_{10}$=C$_2$H$_5$), b.p. 107° C., 0.08 mm. of Hg.

(b) 1.79 gram of a 60% sodium hydride-in-oil suspension is slowly added to a solution of 6.86 grams of p-fluorophenyl isothiocyanate and 9.72 grams of the ketoester (20) (A=CH, q=F, R$_{10}$=C$_2$H$_5$) in THF (110 ml). The solution is stirred at room temperature under a nitrogen atmosphere for 23 hours. After the addition of 2.87 ml of methyliodide, the mixture is stirred for another 16 hours. It is then diluted with 500 ml of water and extracted with ether (3×350 ml). The ether solution is dried over magnesium sulfate, filtered and evaporated under reduced pressure to dryness to give an oil. Purification on a silica gel column yields 8.5 grams enaminoketoester (22) (A=CH, q=F, R$_{10}$=C$_2$H$_5$, R=p-fluorophenyl).

To a cold solution of 5.43 grams of the preceding product (22), (A=CH, q=F, R$_{10}$=C$_2$H$_5$, R=p-fluorophenyl) in 60 ml tetrahydrofuran is slowly added 553 mg of a 60% sodium hydride-in-oil suspension. It is heated at 67° C. for seven hours. It is cooled and the mixture is evaporated to dryness. The residue is dissolved in methylene chloride and washed with water. The organic layer is dried over magnesium sulfate, filtered and evaporated to dryness. Then, 40 ml of an ether/hexane mixture is added to the solid, and it is filtered yielding 2.9 grams of ethyl-1-p-fluorophenyl-6,7-difluoro-2-methylthio-1,4-dihydro-4-oxo-quinoline-3-carboxylate (12) (A=CH, L=F, R$_{10}$=C$_2$H$_5$, R$_{11}$=CH$_3$, R=p-fluorophenyl), m.p. 167° C.

(c) Alternatively, 4.5 grams of a 60% sodium hydride-in-oil suspension is slowly added to a solution of 10.9 grams of the methyl iminochlorothioformate (23) (R=p-fluorophenyl, R$_{11}$=CH$_3$) and 13.7 grams of the ketoester (20) (A=CH, q=F, R$_{10}$=C$_2$H$_5$), in THF (400 ml). The mixture is heated at 60° C. for 24 hours and cooled. The mixture is evaporated to dryness. The residue is dissolved in methylene chloride and washed. The organic layer is dried and evaporated to dryness yielding (12) (A=CH, L=F, R$_{10}$=R=C$_2$H$_5$, R$_{11}$=CH$_3$, R=p-fluorophenyl), m.p. 167° C.

EXAMPLE 37

In the described fashion as Example 36(c), replacing methyl-N-p-fluorophenyl iminochlorothioformate (23) (R=p-fluorophenyl, R$_{11}$=CH$_3$) with phenyl N-substituted iminochlorothioformate (23) where R$_{11}$ is phenyl and R is cyclopropyl, ethyl, or N-formyl-N-methylamino; or in the described fashion as Example 36(b), replacing p-fluorophenyl-isothiocyanate with cyclopropyl isothiocyanate, ethyl isothiocyanate, N-formyl-N-methylamino isothiocyanate or o,p-difluorophenyl isothiocyanate, one can obtain the following compounds:

(a) Ethyl 1-cyclopropyl-2-methylthio-6,7-difluoro-1,4-dihydro-4-oxo-quinoline-3-carboxylate (12) (A=CH, L=F, R$_{10}$=C$_2$H$_5$, R$_{11}$=CH$_3$, R=cyclopropyl), m.p. 137.5° C.

(b) Ethyl 1-ethyl-2-methylthio-6,7-difluoro-1,4-dihydro-4-oxo-quinoline-3-carboxylate (12) (A=CH, L=F, R$_{10}$=C$_2$H$_5$, R$_{11}$=CH$_3$, R=C$_2$H$_5$,), m.p. 113° C.

(c) Ethyl 1-N-formyl-N-methylamino-2-phenylthio-6,7-difluoro-1,4-dihydro-4-oxo-quinoline-3-carboxylate (12) (A=CH, L=F, R$_{10}$=C$_2$H$_5$, R$_{11}$=C$_6$H$_5$, R=N(CH$_3$)CHO).

(d) Ethyl 1-o,p-difluorophenyl-2-methylthio-6,7-difluoro-1,4-dihydro-4-oxo-quinoline-3-carboxylate (12) (A=CH, L=F, R$_{10}$=C$_2$H$_5$, R$_{11}$=C$_6$H$_5$, R=o,p-difluorophenyl).

EXAMPLE 38

In the described fashion as Example 36(a), replacing 2,4,5-trifluorobenzoic acid (18) (A=CH, q=F) with 2,3,4,5-tetrafluorobenzoic acid (18) (A=CF, q=F), 3-chloro-2,4,5-trifluorobenzoic acid (18) (A=CCl, q=F) or 2,6-dichloro-5-fluoronicotinic acid (18) (A=N, q=Cl), one can obtain the following compounds:

(a) Ethyl 2,3,4,5-tetrafluorobenzoylacetate (20). (A=CF, q=F, R$_{10}$=C$_2$H$_5$), m.p. 41°–44° C.

(b) Ethyl 3-chloro-2,4,5-trifluorobenzoylacetate (20) (A=CCl, q=F, R$_{10}$=C$_2$H$_5$).

(c) Ethyl 2,6-dichloro-5-fluoronicotinylacetate (20) (A=N, q=Cl, R$_{10}$=C$_2$H$_5$), m.p. 64°–65° C.

EXAMPLE 39

The compounds (12) listed in 39(a)–(l) can be prepared following the procedures outlined in Examples 36(b) or (c), but replace the ethyl 2,4,5-trifluorobenzoylacetate (20) (A=CH, q=F, R$_{10}$=C$_2$H$_5$) with the compound (20) of either Example 38(a) (A=CF, q=F, R$_{10}$=C$_2$H$_5$), Example 38(b) (A=CCl, q=F, R$_{10}$=C$_2$H$_5$), or Example 38(c) (A=N, q=Cl, R$_{10}$=C$_2$H$_5$). Then react the desired compound (20) with the compound (23) of Example 36(c) or with a phenyl N-substituted iminochlorothioformate compound (23) where R$_{11}$ is phenyl, and R is cyclopropyl, ethyl, or o,p-difluorophenyl. Alternatively, using the p-fluorophenyl isothiocyanate of Example 36(b) or replacing it with cyclopropyl isothiocyanate, ethyl isothiocyanate or o,p-difluorophenyl isothiocyanate, one can prepare compound 12 according to the procedure in Example 36(b).

(a) Ethyl 1-p-fluorophenyl-2-methylthio-6,7,8-trifluoro-1,4-dihydro-4-oxo-quinoline-3-carboxylate (12) (A=CF, L=F, R$_{10}$=C$_2$H$_5$, R$_{11}$=CH$_3$, R=p-fluorophenyl).

(b) Ethyl 1-cyclopropyl-2-phenylthio-6,7,8-trifluoro-1,4-dihydro-4-oxo-quinoline-3-carboxylate (12) (A=CF, L=F, R$_{10}$=C$_2$H$_5$, R$_{11}$=C$_6$H$_5$, R=cyclopropyl), m.p. 135°–137° C.

(c) Ethyl 1-ethyl-2-phenylthio-6,7,8-trifluoro-1,4-dihydro-4-oxo-quinoline-3-carboxylate (12) (A=CF, L=F, R$_{10}$=C$_2$H$_5$, R$_{11}$=C$_6$H$_5$, R=C$_2$H$_5$), m.p. 91° C.

(d) Ethyl 1-o,p-difluorophenyl-2-methylthio-6,7,8-trifluoro-1,4-dihydro-4-oxo-quinoline-3-carboxylate (12) (A=CF, L=F, R$_{10}$=C$_2$H$_5$, R$_{11}$=CH$_3$, R=o,p-difluorophenyl).

(e) Ethyl 1-p-fluorophenyl-2-methylthio-6,7-difluoro-8-chloro-1,4-dihydro-4-oxo-quinoline-3-carboxylate (12) (A=CCl, L=F, R$_{10}$=C$_2$H$_5$, R$_{11}$=CH$_3$, R=p-fluorophenyl).

(f) Ethyl 1-cyclopropyl-2-phenylthio-6,7-difluoro-8-chloro-1,4-dihydro-4-oxo-quinoline-3-carboxylate (12) (A=CCl, L=F, R$_{10}$=C$_2$H$_5$, R$_{11}$=C$_6$H$_5$, R=cyclopropyl).

(g) Ethyl 1-ethyl-2-phenylthio-6,7-difluoro-8-chloro-1,4-dihydro-4-oxo-quinoline-3-carboxylate (12) (A=CCl, L=F, R$_{10}$=C$_2$H$_5$, R$_{11}$=C$_6$H$_5$, R=C$_2$H$_5$).

(h) Ethyl 1-o,p-difluorophenyl-2-methylthio-6,7-difluoro-8-chloro-1,4-dihydro-4-oxo-quinoline-3-carboxylate (12) (A=CCl, L=F, R$_{10}$=C$_2$H$_5$, R$_{11}$=CH$_3$, R=o,p-difluorophenyl).

(i) Ethyl 1-p-fluorophenyl-2-methylthio-6-fluoro-7-chloro-1,4-dihydro-4-oxo-1,8-naphthyridine-3-carboxylate (12) (A=N, L=Cl, $R_{10}=C_2H_5$, $R_{11}=CH_3$, R=p-fluorophenyl), m.p. 176° C.

(j) Ethyl 1-cyclopropyl-2-phenylthio-6-fluoro-7-chloro-1,4-dihydro-4-oxo-1,8-naphthyridine-3-carboxylate (12) (A is N, L=Cl, $R_{10}=C_2H_5$, $R_{11}=C_6H_5$, R=cyclopropyl).

(k) Ethyl 1-ethyl-2-phenylthio-6-fluoro-7-chloro-1,4-dihydro-4-oxo-1,8-naphthyridine-3-carboxylate (12) (A is N, L=Cl, $R_{10}=C_2H_5$, $R_{11}=C_6H_5$, R=$C_2H_5$).

(l) Ethyl 1-o,p-difluorophenyl-2-methylthio-6-fluoro-7-chloro-1,4-dihydro-4-oxo-1,8-naphthyridine-3-carboxylate (12) (A is N, L=Cl, $R_{10}=C_2H_5$, $R_{11}=CH_3$, R=o,p-difluorophenyl).

EXAMPLE 40

Ethyl 1-Cyclopropyl-2-methylthio-6-fluoro-7-acetyl-1,4-dihydro-4-oxo-3-carboxylate t-Butyllithium (6.25 ml, 1.6M in n-pentane) is added dropwise to a solution of methyl vinyl ether (0.92 g) in dry tetrahydrofuran at −65° C. under nitrogen. After removal of the cooling bath, the yellow precipitate redissolves, and the solution becomes colorless between −5 and 0° C. This solution, which contains quantitatively alpha-methoxyvinyllithium (8) is added dropwise to a solution of 3.39 grams of ethyl 1-cyclopropyl-2-methylthio-6,7-difluoro-1,4-dihydro-4-oxo-3-carboxylate (12) of Example 37(a) (A=CH, L=F, $R_{10}=C_2H_5$, $R_{11}=CH_3$, R=cyclopropyl) in 20 ml of tetrahydrofuran at −65° C. Half an hour after the addition, the dry ice bath is removed, and the solution is warmed slowly to room temperature. The solvent is removed, and the crude residue is dissolved in 30 ml of aqueous methanolic 0.02N HCl solution. After 30 minutes, the solvent is removed and the residue is dissolved in methylene chloride (300 ml) and washed with water twice. The organic solvent is dried and evaporated to dryness yielding ethyl 1-cyclopropyl-2-methylthio-6-fluoro-7-acetyl-1,4-dihydro-4-oxo-3-carboxylate (13) (A=CH, $R_{11}=CH_3$, $R_{10}=C_2H_5$, R=cyclopropyl).

EXAMPLE 41

In the described fashion as Example 40, replacing the compound (12) of Example 37(a) (A=CH, L=F, $R_{10}=C_2H_5$, $R_{11}=CH_3$, R=cyclopropyl) with compound (12) of Examples 36, 37(b-d) or of Examples 39(a-l), one can obtain the following compounds:

(a) Ethyl 1-p-fluorophenyl-2-methylthio-6-fluoro-7-acetyl-1,4-dihydro-4-oxo-3-carboxylate (13) (A=CH, $R_{11}=CH_3$, $R_{10}=C_2H_5$, R=p-fluorophenyl).

(b) Ethyl 1-ethyl-2-methylthio-6-fluoro-7-acetyl-1,4-dihydro-4-oxo-3-carboxylate (13) (A=CH, $R_{11}=CH_3$, $R_{10}=C_2H_5$, R=$C_2H_5$).

(c) Ethyl 1-N-formyl-N-methylamino-2-phenylthio-6-fluoro-7-acetyl-1,4-dihydro-4-oxo-3-carboxylate (13). (A=CH, $R_{11}=C_6H_5$, $R_{10}=C_2H_5$, R=N-$CH_3$CHO).

(d) Ethyl 1-o,p-difluorophenyl-2-methylthio-6-fluoro-7-acetyl-1,4-dihydro-4-oxo-3-carboxylate (13) (A=CH, $R_{11}=CH_3$, $R_{10}=C_2H_5$, R=o,p-difluorophenyl).

(e) Ethyl 1-p-fluorophenyl-2-methylthio-6,8-difluoro-7-acetyl-1,4-dihydro-4-oxo-3-carboxylate (13) (A=CF, $R_{11}=CH_3$, $R_{10}=C_2H_5$, R=p-fluorophenyl).

(f) Ethyl 1-cyclopropyl-2-phenylthio-6,8-difluoro-7-acetyl-1,4-dihydro-4-oxo-quinoline-3-carboxylate (13) (A=CF, $R_{11}=C_6H_5$, $R_{10}=C_2H_5$, R=cyclopropyl).

(g) Ethyl 1-ethyl-2-phenylthio-6,8-difluoro-7-acetyl-1,4-dihydro-4-oxo-quinoline-3-carboxylate (13) (A=CF, $R_{11}=C_6H_5$, $R_{10}=C_2H_5$, R=$C_2H_5$,).

(h) Ethyl 1-o,p-difluorophenyl-2-methylthio-6,8-difluoro-7-acetyl-1,4-dihydro-4-oxo-quinoline-3-carboxylate (13) (A=CF, $R_{11}=CH_3$, $R_{10}=C_2H_5$, R=o,p-difluorophenyl.

(i) Ethyl 1-p-fluorophenyl-2-methylthio-6-fluoro-7-acetyl-8-chloro-1,4-dihydro-4-oxo-quinoline-3-carboxylate (13) (A=CCl, $R_1=CH_3$, $R_{10}=C_2H_5$, R=p-fluorophenyl).

(j) Ethyl 1-cyclopropyl-2-phenylthio-6-fluoro-7-acetyl-8-chloro-1,4-dihydro-4-oxo-quinoline-3-carboxylate (13) (A=CCl, $R_{11}=C_6H_5$, $R_{10}=C_2H_5$, R=cyclopropyl).

(k) Ethyl 1-ethyl-2-phenylthio-6-fluoro-7-acetyl-8-chloro-1,4-dihydro-4-oxo-quinoline-3-carboxylate (13) (A=CCl, $R_{11}=C_6H_5$, $R_{10}=C_2H_5$, R=$C_2H_5$).

(l) Ethyl 1-o,p-difluorophenyl-2-methylthio-6-fluoro-7-acetyl-8-chloro-1,4-dihydro-4-oxo-quinoline-3-carboxylate (13) (A=CCl, $R_{11}=CH_3$, $R_{10}=C_2H_5$, R=o,p-difluorophenyl).

(m) Ethyl 1-p-fluorophenyl-2-methylthio-6-fluoro-7-acetyl-1,4-dihydro-4-oxo-1,8-naphthyridine-3-carboxylate (13) A=N, $R_{11}=CH_3$, $R_{10}=C_2H_5$, R=p-fluorophenyl).

(n) Ethyl 1-cyclopropyl-2-phenylthio-6-fluoro-7-acetyl-1,4-dihydro-4-oxo-1,8-naphthyridine-3-carboxylate (13) (A N, $R_{11}=C_6H_5$, $R_{10}=C_2H_5$, R=cyclopropyl).

(o) Ethyl 1-ethyl-2-phenylthio-6-fluoro-7-acetyl-1,4-dihydro-4-oxo-1,8-naphthyridine-3-carboxylate (13) (A=N, $R_{11}=C_6H_5$, $R_{10}=C_2H_5$, R=$C_2H_5$).

(p) Ethyl 1-o,p-difluorophenyl-2-methylthio-6-fluoro-7-acetyl-1,4-dihydro-4-oxo-1,8-naphthyridine-3-carboxylate (13) (A=N, $R_{11}=CH_3$, $R_{10}=C_2H_5$, R=o,p-difluorophenyl).

EXAMPLE 42

Ethyl 1-Cyclopropyl-2-methylthio-6-fluoro-7-(4-N-t-carbobutoxyaminocyclohexyl)-1,4-dihydro-4-oxo-quinoline-3-carboxylate (a) In the described fashion as Example 16 (d and e), replacing ethyl 1-ethyl-6-fluoro-7-acetyl-1,4-dihydro-4-oxo-quinoline carboxylate (9) (A=CH, $R_{10}=C_2H_5$, R=$C_2H_5$,) with ethyl 1-cyclopropyl-2-methylthio-6-fluoro-7-acetyl-1,4-dihydro-4-oxo-3-carboxylate (13) of Example 40 and also replacing the catalyst Raney nickel in Example 16(e) with palladium on charcoal under a hydrogen atmosphere, one can obtain the ethyl 1-cyclopropyl-2-methylthio-6-fluoro-7-(4 aminocyclohexyl)-1,4-dihydro-4-oxo-quinoline-3-carboxylate (16) (A=CH, $R_{11}=CH_3$, $R_{10}=C_2H_5$, R=cyclopropyl, Z=

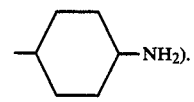

).

(b) To a solution of 4.2 grams of the above compound (16) (A=CH, $R_{11}=CH_3$, $R_{10}=C_2H_5$, R=cyclopropyl, Z=4-aminocyclohexyl) and 2.8 ml of triethylamine in 150 ml methylene chloride in an ice bath is added 2.2 grams of di-t-butyl dicarbonate. After the addition, the ice bath is removed. After six hours, the solution is diluted with 300 ml of methylene chloride, and the organic solution is washed with saturated sodium chloride solution. The organic phase is separated and dried. Evaporation under reduced pressure yields ethyl-1-cyclopropyl-2-methylthio-6-fluoro-7-(4-N-t-carbobutoxyaminocyclohexyl)-1,4-dihydro-4-oxo-quinoline-3-carboxylate (16) (A=CH, $R_{11}$=CH$_3$, $R_{10}$=C$_2$H$_5$, R=cyclopropyl, Z=

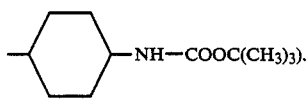

EXAMPLE 43

In the described fashion as Example 42, replacing 1-cyclopropyl-2-methylthio-6-fluoro-7-acetyl-1,4-dihydro-4-oxo-3-carboxylate (13) of Example (4) with other 3-carboxylates (13) of Example 41(a-p), one can obtain the following compounds:

(a) Ethyl 1-p-fluorophenyl-2-methylthio-6-fluoro-7-(4-N-t-carbobutoxyaminocyclohexyl)-1,4-dihydro-4-oxo-quinoline-3-carboxylate (16) (A=CH, $R_{11}$=CH$_3$, $R_{10}$=C$_2$H$_5$, R=p-fluorophenyl, Z=

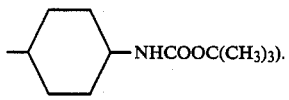

(b) Ethyl 1-ethyl-2-methylthio-6-fluoro-7-(4-N-t-carbobutoxyaminocyclohexyl)-1,4-dihydro-4-oxo-3-carboxylate (16) (A=CH, $R_{11}$=CH$_3$, $R_{10}$=C$_2$H$_5$, R=C$_2$H$_5$, Z=

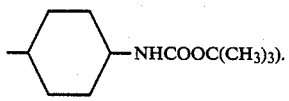

(c) Ethyl 1-N-formyl-N-methylamino-2-phenylthio-6-fluoro-7-(4-N-t-carbobutoxyaminocyclohexyl)-1,4-dihydro-4-oxo-3-carboxylate (16). (A=CH, $R_{11}$=C$_6$H$_5$, $R_{10}$=C$_2$H$_5$, R=N-CH$_3$CHO, Z=

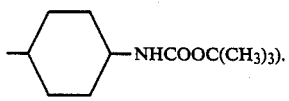

(d) Ethyl 1-o,p-difluorophenyl-2-methylthio-6-fluoro-7-(4-N-t-carbobutoxyaminocyclohexyl)-1,4-dihydro-4-oxo-3-carboxylate (16) (A=CH, $R_{11}$=CH$_3$, $R_{10}$=C$_2$H$_5$, R=o,p-difluorophenyl, Z=

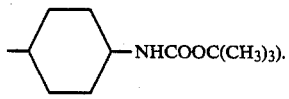

(e) Ethyl 1-p-fluorophenyl-2-methylthio-6,8-difluoro-7-(4-N-t-carbobutoxyaminocyclohexyl)-1,4-dihydro-4-oxo-3-carboxylate (16) (A=CF, $R_{11}$=CH$_3$, $R_{10}$=C$_2$H$_5$, R=p-fluorophenyl, Z=

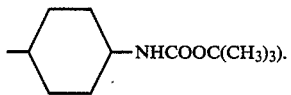

(f) Ethyl 1-cyclopropyl-2-phenylthio-6,8-difluoro-7-(4-N-t-carbobutoxyaminocyclohexyl)-1,4-dihydro-4-oxo-quinoline-3-carboxylate (16) (A=CF, $R_{11}$=C$_6$H$_5$, $R_{10}$=C$_2$H$_5$, R=cyclopropyl, Z=

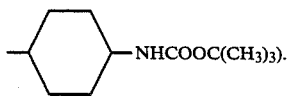

(g) Ethyl 1-ethyl-2-phenylthio-6,8-difluoro-7-(4-N-t-carbobutoxyaminocyclohexyl)-1,4-dihydro-4-oxo-quinoline-3-carboxylate (16) (A=CF, $R_{11}$=C$_6$H$_5$, $R_{10}$=C$_2$H$_5$, R=C$_2$H$_5$, Z=

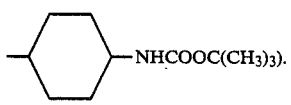

(h) Ethyl 1-o,p-difluorophenyl-2-methylthio-6,8-difluoro-7-(4-N-t-carbobutoxyaminocyclohexyl)-1,4-dihydro-4-oxo-quinoline-3-carboxylate (16) (A=CF, $R_{11}$=CH$_3$, $R_{10}$=C$_2$H$_5$, R=o,p-difluorophenyl, Z=

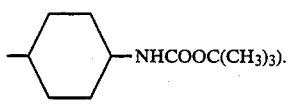

(i) Ethyl 1-p-fluorophenyl-2-methylthio-6-fluoro-7-(4-N-t-carbobutoxyaminocyclohexyl)-8-chloro-1,4-dihydro-4-oxo-quinoline-3-carboxylate (16) (A=CCl, $R_{11}$=CH$_3$, $R_{10}$=C$_2$H$_5$, R=p-fluorophenyl, Z=

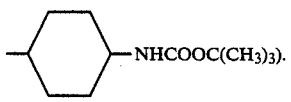

(j) Ethyl 1-cyclopropyl-2-phenylthio-6-fluoro-7-(4-N-t-carbobutoxyaminocyclohexyl)-8-chloro-1,4-dihydro-4-oxo-quinoline-3-carboxylate (16) (A=CCl, $R_{11}$=C$_6$H$_5$, $R_{10}$=C$_2$H$_5$, R=cyclopropyl, Z=

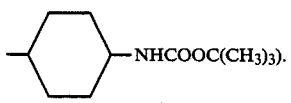

(k) Ethyl 1-ethyl-2-phenylthio-6-fluoro-7-(4-N-t-carbobutoxyaminocyclohexyl)-8-chloro-1,4-dihydro-4-oxo-quinoline-3-carboxylate (16) (A=CCl, $R_{11}$=C$_6$H$_5$, $R_{10}$=C$_2$H$_5$, R=C$_2$H$_5$, Z=

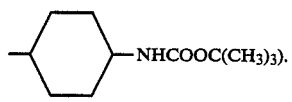

(l) Ethyl 1-o,p-difluorophenyl-2-methylthio-6-fluoro-7-(4-N-t-carbobutoxyaminocyclohexyl)-8-chloro-1,4-dihydro-4-oxo-quinoline-3-carboxylate (16) (A=CCl, $R_{11}$=CH$_3$, $R_{10}$=C$_2$H$_5$, R=o,p-difluorophenyl, Z=

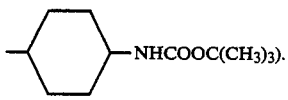

(m) Ethyl 1-p-fluorophenyl-2-methylthio-6-fluoro-7-(4-N-t-carbobutoxyaminocyclohexyl)-1,4-dihydro-4-oxo-1,8-naphthyridine-3-carboxylate (16) (A=N, $R_{11}$=CH$_3$, $R_{10}$=C$_2$H$_5$, R=p-fluorophenyl, Z=

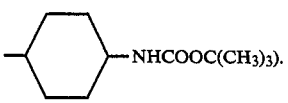

(n) Ethyl 1-cyclopropyl-2-phenylthio-6-fluoro-7-(4-N-t-carbobutoxyaminocyclohexyl)-1,4-dihydro-4-oxo-1,8-naphthyridine-3-carboxylate (16) (A=N, $R_{11}$=C$_6$H$_5$, $R_{10}$=C$_2$H$_5$, R=cyclopropyl, Z=

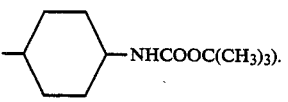

(o) Ethyl 1-ethyl-2-phenylthio-6-fluoro-7-(4-N-t-carbobutoxyaminocyclohexyl)-1,4-dihydro-4-oxo-1,8-naphthyridine-3-carboxylate (16) (A=N, $R_{11}$=C$_6$H$_5$, $R_{10}$=C$_2$H$_5$, R=C$_2$H$_5$, Z=

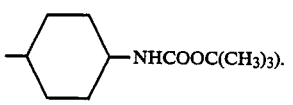

(p) Ethyl 1-o,p-difluorophenyl-2-methylthio-6-fluoro-7-(4-N-t-carbobutoxyaminocyclohexyl)-1,4-dihydro-4-oxo-1,8-naphthyridine-3-carboxylate (16) (A=N, $R_{11}$=CH$_3$, $R_{10}$=C$_2$H$_5$, R=o,p-difluorophenyl, Z=

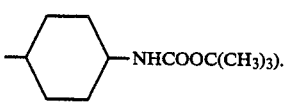

EXAMPLE 44

9-Cyclopropyl-6-fluoro-7-(4-aminocyclohexyl)-2,3,4,9-tetrahydroisoxazolo[5,4-b]quinoline-3,4-dione (a) To a solution of 5.2 grams of ethyl-1-cyclopropyl-2-methylthio-6-fluoro-7-(4-N-t-carbobutoxyaminocyclohexyl)-1,4-dihydro-4-oxo-quinoline-3-carboxylate (16) (A=CH, $R_{11}$=CH$_3$, $R_{10}$=C$_2$H$_5$, R=cyclopropyl, Z=

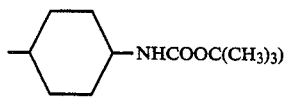

in 100 ml of methylene chloride is added 2.2 grams of 80% meta-chloroperbenzoic acid. After stirring at 25° C. for six hours, the solution is diluted with 300 ml of methylene chloride and washed with dilute sodium bicarbonate solution. The organic solvent is dried over magnesium sulfate and evaporated to dryness yielding the sulfoxide (17) (A=CH, $R_{11}$=CH$_3$, $R_{10}$=C$_2$H$_5$, R=cyclopropyl, Z=

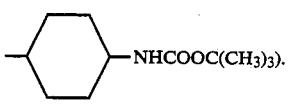

(b) To a solution of 2.7 grams of the above sulfoxide (17) in 40 ml of THF and 40 ml of methanol in an ice bath is added 0.38 gram of hydroxyurea and 1.52 grams of 1,8-diazabicyclo[5,4.0]undec-7-ene (DBU). After one-half hour, the ice bath is removed and the mixture is allowed to stir for an additional 1½ hours. The solvent is evaporated, and the residue is dissolved in 500 ml of water and extracted with 150 ml of ether. The aqueous portion is acidified with acetic acid to pH 7. The precipitate is collected by filtration to yield 9-cyclopropyl-6-fluoro-7-(4-N-t-carbobutoxyaminocyclohexyl)-2,3,4,9-tetrahydroisoxazolo[5,4-b]quinoline-3,4-dione (I) (A=CH, R=Cyclopropyl, $R_3$-$R_1$=ONH, Z=

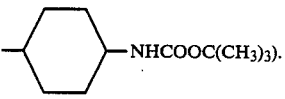

(c) 1.14 grams of the above (I) is dissolved in 5 ml trifluoroacetic acid. After one hour, the solvent is evaporated to dryness yielding the trifluoroacetic acid salt of 9-cyclopropyl-6-fluoro-7-(4-aminocyclohexyl)-2,3,4,9-tetrahydroisoxazolo[5,4-b]quinoline-3,4-dione (I) (A=CH, R=cyclopropyl, $R_3$-$R_1$=ONH, Z=

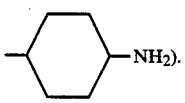

This compound can also be converted into the hydrochloride salt by dissolving 712 mg of the above (I) in 40 ml of water containing 3 ml of 1N hydrochloric acid. This solution is freeze dried to yield the hydrochloride salt of 9-cyclopropyl-6-fluoro-7-(4-aminocyclohexyl)-2,3,4,9-tetrahydroisoxazolo[5,4-b]-quinoline-3,4-dione (I).

EXAMPLE 45

In the described fashion as Example 44, replacing ethyl 2-methylthio-6-fluoro-7-(4-N-t-carbobutoxyaminocyclohexyl)-1,4-dihydro-4-oxo-quinoline-3-carboxylate (16) (A=CH, R$_{11}$=CH$_3$, R$_{10}$=C$_2$H$_5$, R=cyclopropyl, Z=

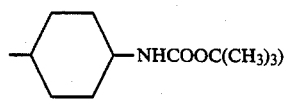

with the 3-carboxylates (16) of Example 43 (a-p), one can obtain the following compounds and their hydrochloride salts:

(a) 9-p-Fluorophenyl-6-fluoro-7-(4-aminocyclohexyl)-2,3,4,9-tetrahydroisoxazolo[5,4-b]quinoline-3,4-dione (I) (A=CH, R=p-fluorophenyl, R$_3$-R$_1$=ONH, Z=

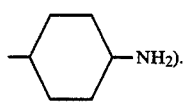

(b) 9-Ethyl-6-fluoro-7-(4-aminocyclohexyl)-2,3,4,9-tetrahydroisoxazolo[5,4-b]quinoline-3,4-dione (I) (A=CH, R=ethyl, R$_3$-R$_1$=ONH, Z=

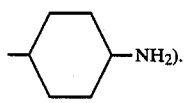

(c) 9-Methylamino-6-fluoro-7-(4-aminocyclohexyl)2,3,4,9-tetrahydroisoxazolo[5,4-b]quinoline-3,4-dione (I) (A=CH, R=NHCH$_3$, R$_3$-R$_1$=ONH, Z=

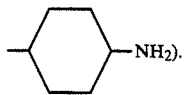

(d) 9-o,p-Difluorophenyl-6-fluoro-7-(4-aminocyclohexyl)-2,3,4,9-tetrahydroisoxazolo[5,4-b]quinoline-3,4-dione (I) (A=CH, R=o,p-difluorophenyl, R$_3$-R$_1$=ONH, Z=

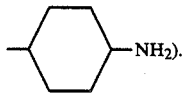

(e) 9-p-Fluorophenyl-6,8-difluoro-7-(4-aminocyclohexyl)-2,3,4,9-tetrahydroisoxazolo[5,4-b]quinoline-3,4-dione (I) (A=CF, R=p-fluorophenyl, R$_3$-R$_1$=ONH, Z=

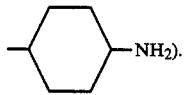

(f) 9-Cyclopropyl-6,8-difluoro-7-(4-aminocyclohexyl)-2,3,4,9-tetrahydroisoxazolo[5,4-b]quinoline-3,4-dione (I) (A=CF, R=cyclopropyl, R$_3$-R$_1$=ONH, Z=

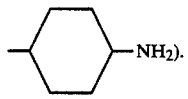

(g) 9-Ethyl-6,8-difluoro-7-(4-aminocyclohexyl)-2,3,4,9-tetrahydroisoxazolo[5,4-b]quinoline-3,4-dione (I) (A=CF, R=ethyl, R$_3$-R$_1$=ONH, Z=

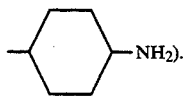

(h) 9-o,p-Difluorophenyl-6,8-difluoro-7-(4-aminocyclohexyl)-2,3,4,9-tetrahydroisoxazolo[5,4-b]quinoline-3,4-dione (I), (A=CF, R=o,p-difluorophenyl, R$_3$-R$_1$=ONH, Z=

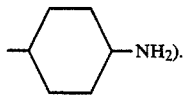

(i) 9-p-Fluorophenyl-6-fluoro-7-(4-aminocyclohexyl)-8-chloro-2,3,4,9-tetrahydroisoxazolo[5,4-b]quinoline-3,4-dione (I) (A=CCl, R=p-fluorophenyl, R$_3$-R$_1$=ONH, Z=

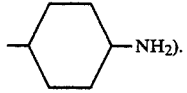

(j) 9-Cyclopropyl-6-fluoro-7-(4-aminocyclohexyl)-8-chloro-2,3,4,9-tetrahydroisoxazolo[5,4-b]quinoline-3,4-dione (I) (A=CCl, R=p-fluorophenyl, R$_3$-R$_1$=ONH, Z=

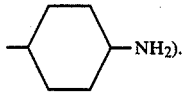

(k) 9-Ethyl-6-fluoro-7-(4-aminocyclohexyl)-8-chloro-2,3,4,9-tetrahydroisoxazolo[5,4-b]quinoline-3,4-dione (I) (A=CCl, R=ethyl, R$_3$-R$_1$=ONH, Z=

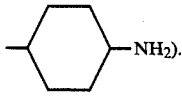

(l) 9-o,p-Difluorophenyl-6-fluoro-7-(4-aminocyclohexyl)-8-chloro-2,3,4,9-tetrahydroisoxazolo[5,4-b]quinoline-3,4-dione (I) (A=CCl, R=o,p-difluorophenyl, R$_3$-R$_1$=ONH, Z=

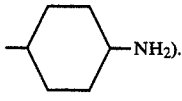

(m) 9-p-Fluorophenyl-6-fluoro-7-(4-aminocyclohexyl)-2,3,4,9-tetrahydroisoxazolo[5,4-b][1,8]naphthyridine-3,4-dione (I) (A=N, R=p-fluorophenyl, R₃-R₁=ONH, Z=

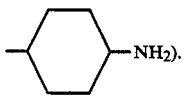

(n) 9-Cyclopropyl-6-fluoro-7-(4-aminocyclohexyl)-2,3,4,9-tetrahydroisoxazolo[5,4-b][1,8]naphthyridine-3,4-dione (I) (A=N, R=cyclopropyl, R₃-R₁=ONH, Z=

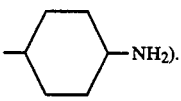

(o) 9-Ethyl-6-fluoro-7-(4-aminocyclohexyl-2,3,4-9-tetrahydroisoxazolo[5,4-b][1,8]naphthyridine-3,4-dione (I) (A=N, R=C₂H₅, R₃-R₁=ONH, Z=

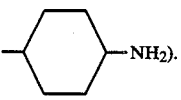

(p) 9-o,p-Difluorophenyl-6-fluoro-7-(4-aminocyclohexyl)-2,3,4,9-tetrahydroisoxazolo[5,4-b][1,8]naphthyridine-3,4-dione (I) (A=N, R=o,p-difluorophenyl, R₃-R₁=ONH, Z=

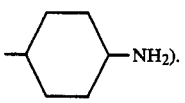

EXAMPLE 46

9-Cyclopropyl-6-fluoro-7-(4-aminocyclohexyl-2,3,4,9-tetrahydroisothiazolo[5,4-b]quinoline-3,4-dione (a) In the described fashion as Example 44(a), using 1-cyclopropyl-2-methylthio-6-fluoro-7-(4-N-t-carbobutoxyaminocyclohexyl)-1,4-dihydro-4-oxo-quinoline-3-carboxylate (16) (A=CH, R₁₁=CH₃, R₁₀=C₂H₅, R=cyclopropyl, Z=

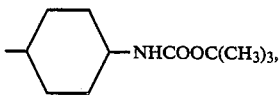

one can obtain the sulfoxide (17) (A=CH, R₁₁=CH₃, R₁₀=C₂H₅, R=cyclopropyl, Z=

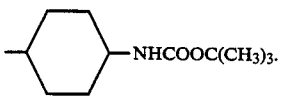

(b) To a solution of 2.7 grams of the sulfoxide (17) in 40 ml of tetrahydrofuran is added 5.45 ml of 0.92N sodium hydrosulfide solution. After the solution is stirred at room temperature for one day, the mixture is evaporated to dryness and redissolved in water (30 ml) containing 580 mg of sodium bicarbonate. The aqueous solution is extracted twice with ether. The aqueous solution is gently heated to evaporate any residual ether and cooled. The solution is acidified with 1N hydrochloric acid to pH 7 and the precipitate is filtered yielding the 2-thiol derivative.

(c) To a solution of 1.06 gram of the preceding compound and 1.4 gram of sodium bicarbonate in 10 ml of tetrahydrofuran and 40 ml of water is added 650 mg of hydroxylamine-0-sulfonic acid. After stirring for three hours, the mixture is filtered and the aqueous portion is diluted with water (20 ml) and extracted with ether (30 ml×2). The aqueous portion is acidified with dilute hydrochloric acid to pH 7 to yield a precipitate. This solid is collected by filtration and combined with the previous solid and is washed with ether to yield the isothiazolo derivative, 9-cyclopropyl-6-fluoro-7-(4-N-t-carbobutoxyaminocyclohexyl)-2,3,4,9-tetrahydroisothiazolo[5,4-b]quinoline-3,4-dione (I) (A=CH, R=cyclopropyl, R₃-R₁=S-NH, Z=

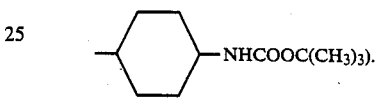

(d) 1.18 gm of the above (I) is dissolved in 65 ml of trifluoroacetic acid. After one hour the solvent is evaporated to dryness yielding the trifluoroacetic acid salt of 9-cyclopropyl-6-fluoro-7-(4-aminocyclohexyl)-2,3,4,9-tetrahydroisothiazolo[5,4-b]quinoline-3,4-dione (I) (A=CH, R=cyclopropyl, R₃-R₁=SNH, Z=

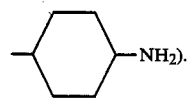

This compound can also be converted into the hydrochloride salt by dissolving 744 mg of the above (I) in 40 ml of water containing 3 ml of 1N hydrochloric acid. This solution is freeze-dried to yield the hydrochloride salt of 9-cyclopropyl-6-fluoro-(4-aminocyclohexyl)-2,3,4,9-tetrahydroisothiazolo[5,4-b]quinoline-3,4-dione (I) (A=CH, R=cyclopropyl, R₃-R₁=SNH, Z=

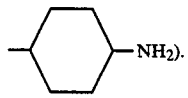

EXAMPLE 47

In the described fashion as Example 46, replacing ethyl 1-cyclopropyl-2-methylthio-6-fluoro-7-(4-N-t-carbobutoxyaminocyclohexyl)-1,4-dihydro-4-oxo-quinoline-3-carboxylate (16) (A=CH, R₁₁=CH₃, R₁₀=C₂H₅, R=cyclopropyl, Z=

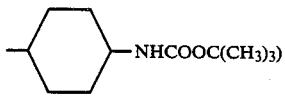

with the 3-carboxylates (16) of Example 43 (a-p), one can obtain the following compounds and their hydrochloride salts.

(a) 9-p-Fluorophenyl-6-fluoro-7-(4-aminocyclohexyl)-2,3,4,9-tetrahydroisothiazolo[5,4-b]quinoline-3,4-dione (I) (A=CH, R=p-fluorophenyl, R$_3$-R$_1$=SNH, Z=

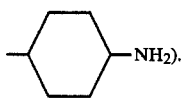

(b) 9-Ethyl-6-fluoro-7-(4-aminocyclohexyl)-2,3,4,9-tetrahydroisothiazolo[5,4-b]quinoline-3,4-dione (I) (A=CH, R=ethyl, R$_3$-R$_1$=SNH, Z=

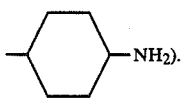

(c) 9-Methylamino-6-fluoro-7-(4-aminocyclohexyl)-2,3,4,9-tetrahydroisothiazolo[5,4-b]quinoline-3,4-dione (I), (A=CH, R-NHCH$_3$, R$_3$-R$_1$=SNH, Z=

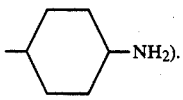

(d) 9-o,p-Difluorophenyl-6-fluoro-7-(4-aminocyclohexyl)-2,3,4,9-tetrahydroisothiazolo[5,4-b]quinoline-3,4-dione (I) (A=CH, R=o,p-difluorophenyl, R$_3$-R$_1$=SNH, Z=

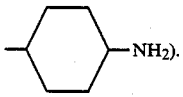

(e) 9-p-Fluorophenyl-6,8-difluoro-7-(4-aminocyclohexyl)-2,3,4,9-tetrahydroisothiazolo[5,4-b]quinoline-3,4-dione (I) (A=CF, R=p-fluorophenyl, R$_3$-R$_1$=SNH, Z=

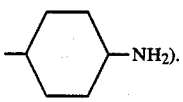

(f) 9-Cyclopropyl-6,8-difluoro-7-(4-aminocyclohexyl)-2,3,4,9-tetrahydroisothiazolo[5,4-b]quinoline-3,4-dione (I) (A-R$_2$=CF, R=cyclopropyl, R$_3$-R$_1$=SNH, Z=

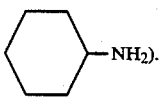

(g) 9-Ethyl-6,8-difluoro-7-(4-aminocyclohexyl)-2,3,4,9-tetrahydroisothiazolo[5,4-b]quinoline-3,4-dione (I) (A=CF, R=ethyl, R$_3$-R$_1$=SNH, Z=

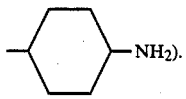

(h) 9-o,p-Difluorophenyl-6,8-difluoro-7-(4-aminocyclohexyl)-2,3,4,9-tetrahydroisothiazolo[5,4-b]quinoline-3,4-dione (I) (A=CF, R=o,p-difluorophenyl, R$_3$-R$_1$=SNH, Z=

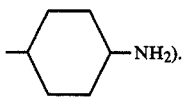

(i) 9-p-Fluorophenyl-6-fluoro-7-(4-aminocyclohexyl)-8-chloro-2,3,4,9-tetrahydroisothiazolo[5,4-b]quinoline-3,4-dione (I) (A=CCl, R=p-fluorophenyl, R$_3$-R$_1$=SNH, Z=

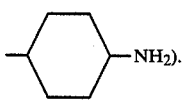

(j) 9-Cyclopropyl-6-fluoro-7-(4-aminocyclohexyl)-8-chloro-2,3,4,9-tetrahydroisothiazolo[5,4-b]quinoline-3,4-dione (I) (A=CCl, R=cyclopropyl, R$_3$-R$_1$=SNH, Z=

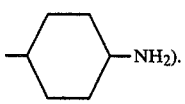

(k) 9-Ethyl-6-fluoro-7-(4-aminocyclohexyl)-8-chloro-2,3,4,9-tetrahydroisothiazolo[5,4-b]quinoline-3,4-dione (I) (A=CCl, R=ethyl, R$_3$-R$_1$=SNH, Z=

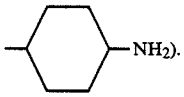

(l) 9-o,p-Difluorophenyl-6-fluoro-7-(4-aminocyclohexyl)-8-chloro-2,3,4,9-tetrahydroisothiazolo[5,4-b]quinoline-3,4-dione (I) (A=CCl, R=o,p-difluorophenyl, R$_3$-R$_1$=SNH, Z=

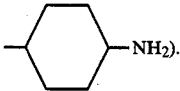

(m) 9-p-Fluorophenyl-6-fluoro-7-(4-aminocyclohexyl)-2,3,4,9-tetrahydroisothiazolo[5,4-b][1,8]naphthyridine-3,4-dione (I) (A=N, R=p-fluorophenyl, R$_3$-R$_1$=SNH, Z=

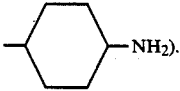

(n) 9-Cyclopropyl-6-fluoro-7-(4-aminocyclohexyl)-2,3,4,9-tetrahydroisothiazolo[5,4-b][1,8]naphthyridine-3,4-dione (I) (A=N, R=cyclopropyl, $R_3$-$R_1$=SNH, Z=

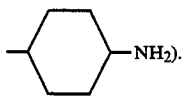

(o) 9-Ethyl-6-fluoro-7-(4-aminocyclohexyl)-2,3,4,9-tetrahydroisothiazolo[5,4-b][1.8]naphthyridine-3,4-dione (I) (A=N, R=$C_2H_5$, $R_3$-$R_1$=SNH, Z=

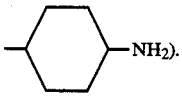

(p) 9-o,p-Difluorophenyl-6-fluoro-7-(4-aminocyclohexyl)-2,3,4,9-tetrahydroisothiazolo[5,4-b][1.8]naphthyridine-3,4-dione (I) (A=N, R=o,p-difluorophenyl, $R_3$-$R_1$=SNH, Z=

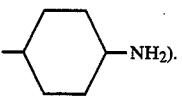

EXAMPLE 48

Ethyl-1-cyclopropyl-2-methylthio-6-fluoro-7-(3-N-t-carbobutoxyaminocyclopentyl)-1,4-dihydro-4-oxo-quinoline-3-carboxylate (a) In the described fashion as Example 21 (b and c), replacing ethyl 1-ethyl-6-fluoro-7-acetyl-1,4-dihydro-4-oxo-quinoline carboxylate (9) (A=CH, $R_{10}$=$C_2H_5$, R=$C_2H_5$) with 1-cyclopropyl-2-methylthio-6-fluoro-7-acetyl-1,4-dihydro-4-oxo-3-carboxylate (13) of Example 40 and also replacing the catalyst Raney nickel catalyst in Example 21(c) with pallidium on carbon under an hydrogen atmosphere, one can obtain ethyl 1-cyclopropyl-2-methylthio-6-fluoro-7-(3-aminocyclopentyl)-1,4-dihydro-4-oxo-quinoline-3-carboxylate (16) (A=CH, $R_{11}$=$CH_3$, $R_{10}$=$C_2H_5$, R=cyclopropyl, Z=

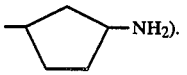

(b) To a solution of 4.0 grams of the above compound (16) (A=CH, $R_{11}$=$CH_3$, $R_{10}$=$C_2H_5$, R=cyclopropyl, Z=3-aminocyclopentyl) and 2.8 ml of triethylamine in 150 ml methylene chloride cooled in an ice bath is added 2.2 grams of di-t-butyl dicarbonate. After the addition, the ice bath is removed, and after six hours, the solution is diluted with 300 ml of methylene chloride. The organic solution is washed with saturated sodium chloride solution. The organic phase is separated and dried. Evaporation under reduced pressure yields ethyl 1-cyclopropyl-2-methylthio-6-fluoro-7-(3-N-t-carbobutoxyaminocyclopentyl)-1,4-dihydro-4-oxo-quinoline-3-carboxylate (16) (A=CH, $R_{11}$=$CH_3$, $R_{10}$=$C_2H_5$, R=cyclopropyl, Z=

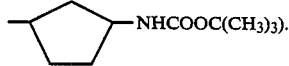

EXAMPLE 49

In the described fashion as Example 48, replacing 1-cyclopropyl-2-methylthio-6-fluoro-7-acetyl-1,4-dihydro-4-oxo-quinoline-3-carboxylate (13) of Example 40 with the 3-carboxylates (13) of Example 41 (a-p), one can obtain the following compounds.

(a) Ethyl 1-p-fluorophenyl-2-methylthio-6-fluoro-7-(3-N-t-carbobutoxyaminocyclopentyl)-1,4-dihydro-4-oxo-quinoline-3-carboxylate (16) (A=CH, $R_{11}$=$CH_3$, $R_{10}$=$C_2H_5$, R=p-fluorophenyl, Z=

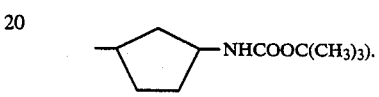

(b) Ethyl 1-ethyl-2-methylthio-6-fluoro-7-(3-N-t-carbobutoxyaminocyclopentyl)-1,4-dihydro-4-oxo-3-carboxylate (16) (A=CH, $R_{11}$=$CH_3$, $R_{10}$=$C_2H_5$, R=$C_2H_5$, Z=

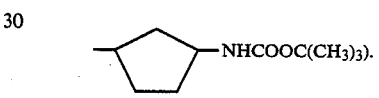

(c) Ethyl 1-N-formyl-N-methylamino-2-phenylthio-6-fluoro-7-(3-N-t-carbobutoxyaminocyclopentyl)-1,4-dihydro-4-oxo-3-carboxylate (16) (A=CH, $R_{11}$=$C_6H_5$, $R_{10}$=$C_2H_5$, R=N-$CH_3$CHO, Z=

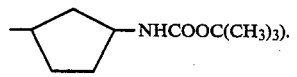

(d) Ethyl 1-o,p-difluorophenyl-2-methylthio-6-fluoro-7-(3-N-t-carbobutoxyaminocyclopentyl)-1,4-dihydro-4-oxo-3-carboxylate (16) (A=CH, $R_{11}$=$CH_3$, $R_{10}$=$C_2H_5$, R=o,p-difluorophenyl, Z=

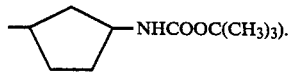

(e) Ethyl 1-p-fluorophenyl-2-methylthio-6,8-difluoro-7-(3-N-t-carbobutoxyaminocyclopentyl)-1,4-dihydro-4-oxo-3-carboxylate (16) (A=CF, $R_{11}$=$CH_3$, $R_{10}$=$C_2H_5$, R=p-fluorophenyl, Z=

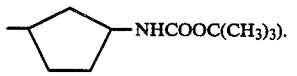

(f) Ethyl-1-cyclopropyl-2-phenylthio-6,8-difluoro-7-(3-N-t-carbobutoxyaminocyclopentyl) 1,4-dihydro-4-oxo-quinoline-3-carboxylate (16) A=CF, $R_{11}$=$C_6H_5$, $R_{10}$=$C_2H_5$, R=cyclopropyl, Z=

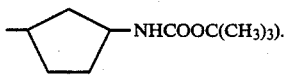

(g) Ethyl 1-ethyl-2-phenylthio-6,8-difluoro-7-(3-N-t-carbobutoxyaminocyclopentyl)-1,4-dihydro-4-oxo-quinoline-3-carboxylate (16) (A=CF, $R_{11}=C_6H_5$, $R_{10}=C_2H_5$, R=$C_2H_5$, Z=

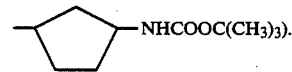

(h) Ethyl 1-o,p-difluorophenyl-2-methylthio-6,8-difluoro-7-(3-N-t-carbobutoxyaminocyclopentyl)-1,4-dihydro-4-oxo-quinoline-3-carboxylate (16) A=CF, $R_{11}=CH_3$, $R_{10}=C_2H_5$, R=o,p-difluorophenyl, Z=

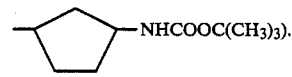

(i) Ethyl 1-p-fluorophenyl-2-methylthio-6-fluoro-7-(3-N-t-carbobutoxyaminocyclopentyl)-8-chloro-1,4-dihydro-4-oxo-quinoline-3-carboxylate (16) (A=CCl, $R_{11}=CH_3$, $R_{10}=C_2H_5$, R=p-fluorophenyl, Z=

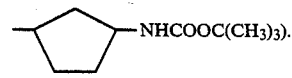

(j) Ethyl 1-cyclopropyl-2-phenylthio-6-fluoro-7-(3-N-t-carbobutoxyaminocyclopentyl)-8-chloro-1,4-dihydro-4-oxo-quinoline-3-carboxylate (16) (A=CCl, $R_{11}=C_6H_5$, $R_{10}=C_2H_5$, R=cyclopropyl, Z=

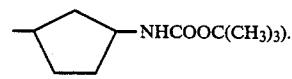

(k) Ethyl 1-ethyl-2-phenylthio-6-fluoro-7-(3-N-t-carbobutoxyaminocyclopentyl)-8-chloro-1,4-dihydro-4-oxo-quinoline-3-carboxylate (16) (A=CCl, $R_{11}=C_6H_5$, $R_{10}=C_2H_5$, R=$C_2H_5$, Z=

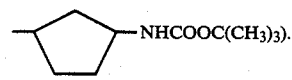

(l) Ethyl 1-o,p-difluorophenyl-2-methylthio-6-fluoro-7-(3-N-t-carbobutoxyaminocyclopentyl)-8-chloro-1,4-dihydro-4-oxo-quinoline-3-carboxylate (16) (A=CCl, $R_{11}=CH_3$, $R_{10}=C_2H_5$, R=o,p-difluorophenyl, Z=

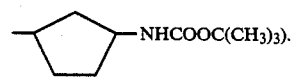

(m) Ethyl 1-p-fluorophenyl-2-methylthio-6-fluoro-7-(3-N-t-carbobutoxyaminocyclopentyl)-1,4-dihydro-4-oxo-1,8-naphthyridine-3-carboxylate (16) (A=N, $R_{11}=CH_3$, $R_{10}=C_2H_5$, R=p-fluorophenyl, Z=

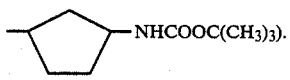

(n) Ethyl 1-cyclopropyl-2-phenylthio-6-fluoro-7-(3-N-t-carbobutoxyaminocyclopentyl)-1,4-dihydro-4-oxo-1,8naphthyridine-3-carboxylate (16) (A=N, $R_{11}=C_6H_5$, $R_{10}=C_2H_5$, R=cyclopropyl, Z=

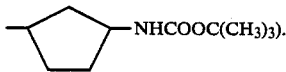

(o) Ethyl 1-ethyl-2-phenylthio-6-fluoro-7-(3-N-t-carbobutoxyaminocyclopentyl)-1,4-dihydro-4-oxo-1,8-naphthyridine-3-carboxylate (16) (A=N, $R_{11}=C_6H_5$, $R_{10}=C_2H_5$, R=$C_2H_5$, Z=

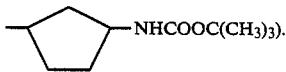

(p) Ethyl 1-o,p-difluorophenyl-2-methylthio-6-fluoro-7-(3-N-t-carbobutoxyaminocyclopentyl)-1,4-dihydro-4-oxo-1,8-naphthyridine-3-carboxylate (16) (A=N, $R_{11}=CH_3$, $R_{10}=C_2H_5$, R=o,p-difluorophenyl, Z=

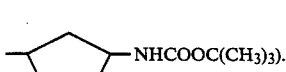

EXAMPLE 50

9-Cyclopropyl-6-fluoro-7-(3-aminocyclopentyl)-2,3,4,9-tetrahydroisoxazolo[5,4-b]quinoline-3,4-dione In the described fashion as Example 44, replacing ethyl-1-cyclopropyl-2-methylthio-6-fluoro-7-(4-N-t-carbobutoxyaminocyclohexyl)-1,4-dihydro-4-oxo-quinoline-3-carboxylate (16) (A=CH, $R_{11}=CH_3$, $R_{10}=C_2H_5$, R=cyclopropyl, Z=

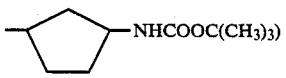

with the carboxylate (16) of Example 48 (A=CH, $R_{11}=CH_3$, $R_{10}=C_2H_5$, R=cyclopropyl, Z=

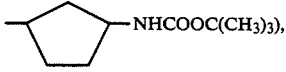

one can obtain 9-cyclopropyl-6-fluoro-7-(3-aminocyclopentyl)-2,3,4,9-tetrahydroisoxazolo[5,4-b]quinoline-3,4-dione (I) and its hydrochloride salt. (A=CH, R=cyclopropyl, $R_3$-$R_1$=OHN, Z=

EXAMPLE 51

In the described fashion as Example 50, replacing ethyl 1-cyclopropyl-2-methylthio-6-fluoro-7-(3-N-t-carbobutoxyaminocyclopentyl)-1,4-dihydro-4-oxo-quinoline-3-carboxylate (16) (A=CH, R₁₁=CH₃, R₁₀=C₂H₅, R=cyclopropyl, Z=

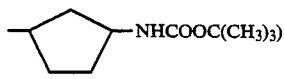

with the 3-carboxylates (16) of Example 49 (a-p), one can obtain the following compounds and their hydrochloride salts.

(a) 9-p-Fluorophenyl-6-fluoro-7-(3-aminocyclopentyl)-2,3,4,9-tetrahydroisoxazolo[5,4-b]quinoline-3,4-dione (I) (A=CH, R=p-fluorophenyl, R₃-R₁=ONH, Z=

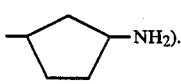

(b) 9-Ethyl-6-fluoro-7-(3-aminocyclopentyl)-2,3,4,9-tetrahydroisoxazolo[5,4-b]quinoline-3,4-dione (I) (A=CH, R=ethyl, R₃-R₁=ONH, Z=

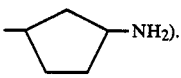

(c) 9-Methylamino-6-fluoro-7-(3-aminocyclopentyl)-2,3,4,9-tetrahydroisoxazolo[5,4-b]quinoline-3,4-dione (I) (A=CH, R=NHCH₃, R₃-R₁=ONH, Z=

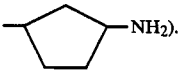

(d) 9-o,p-Difluorophenyl-6-fluoro-7-(3-aminnocyclopentyl)-2,3,4,9-tetrahydroisoxazolo[5,4-b]quinoline-3,4-dione (I) (A=CH, R=o,p-difluorophenyl, R₃-R₁=ONH, Z=

(e) 9-p-Fluorophenyl-6,8-difluoro-7-(3-aminocyclopentyl)-2,3,4,9-tetrahydroisoxazolo[5,4-b]quinoline-3,4-dione (I) (A=CF, R=p-fluorophenyl, R₃-R₁=ONH, Z=

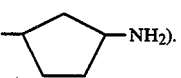

(f) 9-Cyclopropyl-6,8-difluoro-7-(3-aminocyclopentyl)-2,3,4,9-tetrahydroisoxazolo[5,4-b]quinoline-3,4-dione (I) (A=CF, R=cyclopropyl, R₃-R₁=ONH, Z=

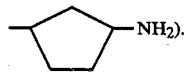

(g) 9-Ethyl-6,8-difluoro-7-(3-aminocyclopentyl)-2,3,4,9-tetrahydroisoxazolo[5,4-b]quinoline-3,4-dione (I) (A=CF, R=ethyl, R₃-R₁=ONH, Z=

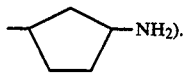

(h) 9-o,p-Difluorophenyl-6,8-difluoro-7-(3-aminocyclopentyl)-2,3,4,9-tetrahydroisoxazolo[5,4-b]quinoline-3,4-dione (I) (A=CF, R=o,p-difluorophenyl, R₃-R₁=ONH, Z=

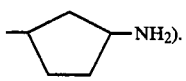

(i) 9-p-Fluorophenyl-6-fluoro-7-(3-aminocyclopentyl)-8-chloro-2,3,4,9-tetrahydroisoxazolo[5,4-b]quinoline-3,4-dione (I) (A=CCl, R=p-fluorophenyl, R₃-R₁=ONH, Z=

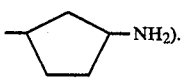

(j) 9-Cyclopropyl-6-fluoro-7-(3-aminocyclypentyl)-8-chloro-2,3,4,9-tetrahydroisoxazolo[5,4-b]quinoline-3,4-dione (I) (A=CCl, R=cyclopropyl, R₃-R₁=ONH, Z=

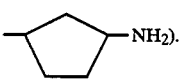

(k) 9-Ethyl-6-fluoro-7-(3-aminocyclopentyl)-8-chloro-2,3,4,9-tetrahydroisoxazolo[5,4-b]quinoline-3,4-dione (I) (A=CCl, R=ethyl, R₃-R₁=ONH, Z=

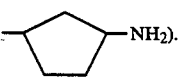

(l) 9-o,p-Difluorophenyl-6-fluoro-7-(3-aminocyclopentyl)-8-chloro-2,3,4,9-tetrahydroisoxazolo[5,4-b]quinoline-3,4-dione (I) (A=CCl, R=o,p-difluorophenyl, R₃-R₁=ONH, Z=

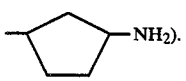

(m) 9-p-Fluorophenyl-6-fluoro-7-(3-aminocyclopentyl)-2,3,4,9-tetrahydroisoxazolo[5,4-b][1,8]naphthyridine-3,4-dione (I) (A=N, R=p-fluorophenyl, R₃-R₁=OHN, Z=

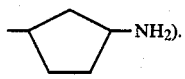

(n) 9-Cyclopropyl-6-fluoro-7-(3-aminocyclopentyl)-2,3,4,9-tetrahydroisoxazolo[5,4-b][1,8]naphthyridine-3,4-dione (I) (A=N, R=cyclopropyl, $R_3$-$R_1$=ONH, Z=

(o) 9-Ethyl-6-fluoro-7-(3-aminocyclopentyl)-2,3,4,9-tetrahydroisoxazolo[5,4-b][1,8]naphthyridine-3,4-dione (I) (A=N, R=$C_2H_5$, $R_3$-$R_1$=ONH, Z=

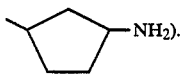

(p) 9-o,p-Difluorophenyl-6-fluoro-7-(3-aminocyclopentyl)-2,3,4,9-tetrahydroisoxazolo[5,4-b][1,8]naphthyridine-3,4-dione (I) (A=N, R=o,p-difluorophenyl, $R_3$-$R_1$=ONH, Z=

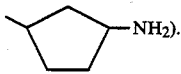

EXAMPLE 52

9-Cyclopropyl-6-fluoro-7-(3-aminocyclopentyl)-2,3,4,9-tetrahydroisothiazolo[5,4-b]quinoline-3,4-dione In the described fashion as Example 46, replacing the 1-cyclopropyl-2-methylthio-6-fluoro-7-(4-N-t-carbobutoxyaminocyclohexyl)1,4-dihydro-4-oxo-quinoline-3-carboxylate (16) (A=CH, $R_{11}$=$CH_3$, $R_{10}$=$C_2H_5$, R=cyclopropyl, Z=

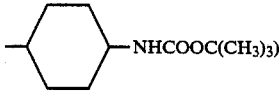

in Example 46(a) with 1-cyclopropyl-2-methylthio-6-fluoro-7-(3-N-t-carbobutoxyaminocyclopentyl)-1,4-dihydro-4-oxo-quinoline-3-carboxylate (16) of Example 48 (A=CH, $R_{11}$=$CH_3$, $R_{10}$=$C_2H_5$, R=cyclopropyl, Z=

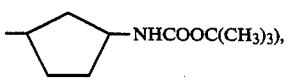

one can obtain 9-cyclopropyl-6-fluoro-7-(3-aminocyclopentyl)-2,3,4,9-tetrahydroisothiazolo[5,4-b]quinoline-3,4-dione (I) and its hydrochloride salt. (A=CH, R=cyclopropyl, $R_3$-$R_1$=SNH, Z=

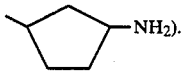

EXAMPLE 53

In the described fashion as Example 52, replacing ethyl-1-cyclopropyl-2-methylthio-6-fluoro-7-(3-N-t-carbobutoxyaminocyclopentyl)-1,4-dihydro-4-oxo-quinoline-3-carboxylate (16) (A=CH, $R_{11}$=$CH_3$, $R_{10}$=$C_2H_5$, R=cyclopropyl, Z=

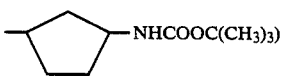

with the 3-carboxylates (16) of Example 49 (a–p), one can obtain the following compounds and their hydrochloride salts.

(a) 9-p-Fluorophenyl-6-fluoro-7-(3-aminocyclopentyl)-2,3,4,9-tetrahydroisothiazolo[5,4-b]quinoline-3,4-dione (I) (A=CH, R=p-fluorophenyl, $R_3$-$R_1$=SNH, Z=

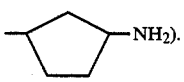

(b) 9-Ethyl-6-fluoro-7-(3-aminocyclopentyl)-2,3,4,9-tetrahydroisothiazolo[5,4-b]quinoline-3,4-dione (I) (A=CH, R=ethyl, $R_3$-$R_1$=SNH, Z=

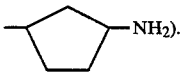

(c) 9-Methylamino-6-fluoro-7-(3-aminocyclopentyl)-2,3,4,9-tetrahydroisothiazolo[5,4-b]quinoline-3,4-dione (I) (A=CH, R=$NHCH_3$, $R_3$-$R_1$=SNH, Z=

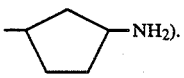

(d) 9-o,p-Difluorophenyl-6-fluoro-7-(3-aminocyclopentyl)-2,3,4,9-tetrahydroisothiazolo[5,4-b]quinoline-3,4-dione (I) (A=CH, R=o,p-difluorophenyl, $R_3$-$R_1$=SNH, Z=

(e) 9-p-Fluorophenyl-6,8-difluoro-7-(3-aminocyclopentyl)-2,3,4,9-tetrahydroisothiazolo[5,4-b]quinoline-3,4-dione (I) (A=CF, R=p-fluorophenyl, $R_3$-$R_1$=SNH, Z=

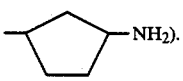

(f) 9-Cyclopropyl-6,8-difluoro-7-(3-aminocyclopentyl)-2,3,4,9-tetrahydroisothiazolo[5,4-b]quinoline-3,4-dione (I) (A=CF, R=cyclopropyl, R₃-R₁=SNH, Z=

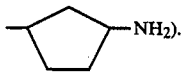

(g) 9-Ethyl-6,8-difluoro-7-(3-aminocyclopentyl)-2,3,4,9-tetrahydroisothiazolo[5,4-b]quinoline-3,4-dione (I) (A=CF, R=ethyl, R₃-R₁=SNH, Z=

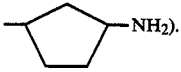

(h) 9-o,p-Difluorophenyl-6,8-difluoro-7-(3-aminocyclopentyl)-2,3,4,9-tetrahydroisothiazolo[5,4-b]quinoline-3,4-dione (I) (A=CF, R=o,p-difluorophenyl, R₃-R₁=SNH, Z=

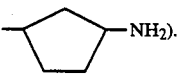

(i) 9-p-Fluorophenyl-6-fluoro-7-(3-aminocyclopentyl)-8-chloro-2,3,4,9-tetrahydroisothiazolo[5,4-b]quinoline-3,4-dione (I) (A=CCl, R=cyclopropyl, R₃-R₁=SNH, Z=

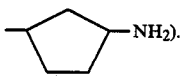

(j) 9-Cyclopropyl-6-fluoro-7-(3-aminocyclopentyl)-8-chloro-2,3,4,9-tetrahydroisothiazolo[5,4-b]quinoline-3,4-dione (I) (A=CCl, R=cyclopropyl, R₃-R₁=SNH, Z=

(k) 9-Ethyl-6-fluoro-7-(3-aminocyclopentyl)-8-chloro-2,3,4,9-tetrahydroisothiazolo[5,4-b]quinoline-3,4-dione (I) (A=CCl, R=ethyl, R₃-R₁=SNH, Z=

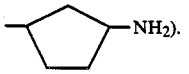

(l) 9-o,p-Difluorophenyl-6-fluoro-7-(3-aminocyclopentyl)-8-chloro-2,3,4,9-tetrahydroisothiazolo[5,4-b]quinoline-3,4-dione (I) (A=CCl, R=o,p-difluorophenyl, R₃-R₁=SNH, Z=

(m) 9-p-Fluorophenyl-6-fluoro-7-(3-aminocyclopentyl)-2,3,4,9-tetrahydroisothiazolo[5,4-b][1,8]naphthyridine-3,4-dione (I) (A=N, R=p-fluorophenyl, R₃-R₁=SNH, Z=

(n) 9-Cyclopropyl-6-fluoro-7-(3-aminocyclopentyl)-2,3,4,9-tetrahydroisothiazolo[5,4-b][1,8]naphthyridine-3,4-dione (I) (A=N, R=cyclopropyl, R₃-R₁=SNH, Z=

(o) 9-Ethyl-6-fluoro-7-(3-aminocyclopentyl)-2,3,4,9-tetrahydroisothiazolo[5,4-b][1,8]naphthyridine-3,4-dione (I) (A=N, R=C₂H₅, R₃-R₁=SNH, Z=

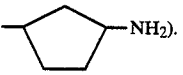

(p) 9-o,p-Difluorophenyl-6-fluoro-7-(3-aminocyclopentyl)-2,3,4,9-tetrahydroisothiazolo[5,4-b][1,8]naphthyridine-3,4-dione (I) (A=N, R=o,p-difluorophenyl, R₃-R₁=SNH, Z=

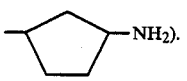

EXAMPLE 54

Ethyl 9,10-difluoro-3-methyl-5-phenylthio-2,3-dihydro-7-oxo-7H-pyrido[1,2,3-de][1,4]benzoxazine-6-carboxylate (a) To a solution of 2.64 grams of ethyl 2,3,4,5-tetrafluorobenzoylacetate (38) (q=F, R₁₀=C₂H₅) of Example 38(a) in 45 ml of toluene at room temperature is added 0.41 gram of a 60% sodium hydride-in-oil suspension. 2.72 grams of the iminochlorothioformate (39) (R₆=CH₃, R₁₁=C₆H₅) is added to the mixture. After stirring for one-half hour, the mixture is heated at reflux for 18 hours. One ml of acetic acid is added to the mixture and the solvent is removed under reduced pressure. The residue is dissolved in methylene chloride (300 ml) and washed with saturated sodium chloride solution. The organic layer is dried and purified by silica gel column chromatography to give 2.5 grams of 1,4-dihydro-4-oxo-quinoline-3-carboxylate (40) (R₆=CH₃, R₁₀=C₂H₅, R₁₁=C₆H₅, q=F).

(b) Two grams of the preceding compound (40) is dissolved in 30 ml acetonitrile. Three ml of 3N hydrochloric acid is added. The mixture is heated at 50° C. for one hour. The solvent is removed under reduced pressure. The residue is dissolved in 400 ml of methylene chloride and washed with saturated sodium chloride solution. The organic layer is dried and concentrated, and the residue is purified to yield the alcohol (41) (R₆=CH₃, R₁₀=C₂H₅, R₁₁=C₆H₅, q=F).

(c) To a solution of 2.2 grams of the preceding alcohol (41) (R₆=CH₃, R₁₀=C₂H₅, R₁₁=C₆H₅, q=F) in 30 ml of THF at 0° C. is added 0.41 gram of a 60% sodium hydride-in-oil suspension. The reaction mixture is heated at 55° C. for 12 hours. Acetic acid (0.5 ml) is added, and the solvent is removed under reduced pressure. The residue is dissolved in 500 ml of methylene chloride and washed with saturated sodium chloride solution. The organic portion is dried and evaporated to dryness. Purification on a silica gel column yields the ethyl 9,10-difluoro-3-methyl-5-phenylthio-2,3-dihydro-7-oxo-7H-pyrido[1,2,3-de][1,4]benzoxazine-6-carboxylate (12) (A-R=COCH$_2$CHCH$_3$, R$_{10}$=C$_2$H$_5$, R$_{11}$=C$_6$H$_5$, L=F).

EXAMPLE 55

Ethyl 9-fluoro-10-acetyl-3-methyl-5-phenylthio-2,3-dihydro-7-oxo-7H-pyrido[1,2,3-de][1,4]benzoxazine-6-carboxylate In the described fashion as Example 40, replacing ethyl 1-cyclopropyl-2-methylthio-6,7-difluoro-1,4-dihydro-4-oxo-3-carboxylate (12) of Example 37(a) with ethyl 9,10-difluoro-3-methyl-5-phenylthio-2,3-dihydro-7-oxo-7H-pyrido[1,2,3-de][1,4]benzoxazine-6-carboxylate (12) of Example 54, one can obtain the ethyl 9-fluoro-10-acetyl-3-methyl-5-phenylthio-2,3-dihydro-7-oxo-7H-pyrido[1,2,3-de][1,4]benzoxazine-6-carboxylate (13) (A-R=COCH$_2$CHCH$_3$, R$_{10}$=C$_2$H$_5$, R$_{11}$=C$_6$H$_5$).

EXAMPLE 56

Ethyl 9-Fluoro-10-(4-N-t-carbobutoxyaminocyclohexyl)-3-methyl-5-phenylthio-2,3-dihydro-7-oxo-7H-pyrido[1,2,3-de][1,4]benzoxazine-6-carboxylate In the described fashion as Example 42, replacing ethyl 1-cyclopropyl-2-methylthio-6-fluoro-7-acetyl-1,4-dihydro-4-oxo-3-carboxylate (13) of Example 40 with ethyl 9-fluoro-10-acetyl-3-methyl-5-phenylthio-2,3-dihydro-7-oxo-7H-pyrido[1,2,3-de][1,4]benzoxazine-6-carboxylate (13) of Example 55, one can obtain ethyl-9-fluoro-10-(4-N-t-carbobutoxyaminocyclohexyl)-3-methyl-5-phenylthio-2,3-dihydro-7-oxo-7H-pyrido[1,2,3-de][1,4]benzoxazine-6-carboxylate (16) (A-R=COCH$_2$CHCH$_3$, R$_{10}$=C$_2$H$_5$, R$_{11}$=C$_6$H$_5$, Z=

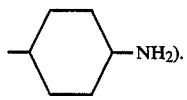.

EXAMPLE 57

1-Methyl-4-(4-aminocyclohexyl)-5-fluoro-1,2,8,9-tetrahydro-7H-isoxazolo[4',5':5,6]pyrido[1,2,3-de][1,4-]benzoxazine-7,8-dione The procedure of Example 44 can be repeated replacing the ethyl 1-cyclopropyl-2-methylthio-6-fluoro-7-4-N-t-carbobutoxyaminocyclohexyl)-1,4-dihydro-4-oxoquinoline-3-carboxylate (16) (A=CH, R$_{11}$=CH$_3$, R$_{10}$=C$_2$H$_5$, R=cyclopropyl, Z=

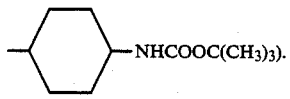, with ethyl 9-fluoro-10-(4-N-t-carbobutoxyaminocyclohexyl)-3-methyl-5-phenylthio-2,3-dihydro-7-oxo-7H-pyrido[1,2,3-de][1,4]benzoxazine-6-carboxylate (16) of Example 56 (A-R=COCH$_2$CHCH$_3$, R$_{10}$=C$_2$H$_5$, R$_{11}$=C$_6$H$_5$, Z=

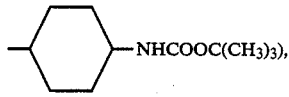

one can obtain 1-methyl-4-(4-aminocyclohexyl)-5-fluoro-1,2,8,9-tetrahydro-7H-isoxazolo[4',5':5,6)-]pyrido[1,2,3-de][1,4]benzoxazine-7,8-dione (I) and its hydrochloride salt. (A-R=COCH$_2$CHCH$_3$, R$_3$-R$_1$-=ONH, Z=

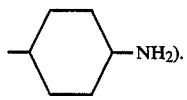.

EXAMPLE 58

1-Methyl-4-(4-aminocyclohexyl)-5-fluoro-1,2,8,9-tetrahydro-7H-isothiazolo[4',5':5,6]pyrido[1,2,3-de][1,4-]benzoxazine-7,8-dione In the described fashion as Example 46, replacing 1-cyclopropyl-2-methylthio-6-fluoro-7-(4-N-t-carbobutoxyaminocyclohexyl)-1,4-dihydro-4-oxo-quinoline-3-carboxylate (A-R$_2$=CH, R$_{11}$=CH$_3$, R$_{10}$=C$_2$H$_5$, R=cyclopropyl, Z=

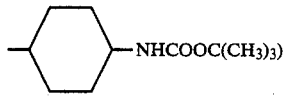

with ethyl 9-fluoro-10-(4-N-t-carbobutoxyaminocyclohexyl)-3-methyl-5-phenylthio-2,3-dihydro-7-oxo-7H-pyrido[1,2,3-de][1,4]benzoxazine-6-carboxylate (16) of Example (56) (A-R=COCH$_2$CHCH$_3$, R$_{10}$=C$_2$H$_5$, R$_{11}$=C$_6$H$_5$, Z=

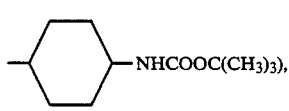, one can obtain 1-methyl-4-(4-aminocyclohexyl)-5-fluoro-1,2,8,9-tetrahydro-7H-isothiazolo[4',5':5,6-]pyrido[1,2,3,-de][1,4]benzoxazine-7,8-dione (I) and its hydrochloride salt (A-R=COCH$_2$CHCH$_3$, R$_3$-R$_1$=SNH, Z=

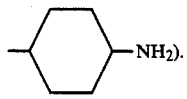.

EXAMPLE 59

Ethyl 9-Fluoro-10-(3-N-t-carbobutoxyaminocyclopentyl)-3-methyl-5-phenylthio-2,3-dihydro-7-oxo-7H-pyrido[1,2,3-de][1,4]benzoxazine-6-carboxylate In the described fashion as Example 48, replacing ethyl 1-cyclopropyl-2-methylthio-6-fluoro-7-acetyl-1,4-dihydro-4-oxo-3-carboxylate (13) of Example 40 with ethyl 9-fluoro-10-acetyl-3-methyl-5-phenylthio-2,3-dihydro-7-oxo-7H-pyrido[1,2,3-de][1,4]benzoxazine-6-carboxylate (13) of Example 55, one can obtain ethyl 9-fluoro-10-(3-N-t-carbobutoxyaminocyclopentyl)-3-methyl-5-phenylthio-2,3-dihydro-7-oxo-7H-pyrido[1,2,3-de][1,4]benzoxazine-6-carboxylate (16) (A-R=COCH$_2$CHCH$_3$, R$_{10}$=C$_2$H$_5$, R$_{11}$=C$_6$H$_5$, Z=

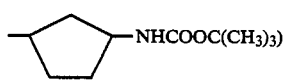

EXAMPLE 60

1-Methyl-4-(3-aminocyclopentyl)-5-fluoro-1,2,8,9-tetrahydro-7H-isoxazolo[4',5':5,6]pyrido[1,2,3-de][1,4]benzoxazine-7,8-dione The procedure of example 50 can be repeated, replacing the ethyl 1-cyclopropyl-2-methylthio-6-fluoro-7-(4-N-t-carbobutoxyaminocyclohexyl)-1,4-dihydro-4-oxo-quinoline-3-carboxylate (16) (A=CH, R$_{11}$=CH$_3$, R$_{10}$=C$_2$H$_5$, R=cyclopropyl, Z=

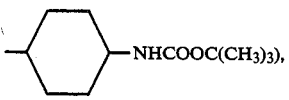

with ethyl 9-fluoro-10-(3-N-t-carbobutoxyaminocyclopentyl)-3-methyl-5-phenylthio-2,3-dihydro-7-oxo-7H-pyrido[1,2,3-de][1,4]benzoxazine-6-carboxylate (16) of Example 59 (A-R=COCH$_2$CHCH$_3$, R$_{10}$=C$_2$H$_5$, R$_{11}$=C$_6$H$_5$, Z=

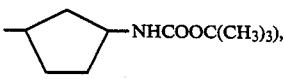

one can obtain 1-methyl-4-(3-aminocyclopentyl)-5-fluoro-1,2,8,9-tetrahydro-7H-isoxazolo[4',5':5,6]pyrido[1,2,3-de][1,4]benzoxazine-7,8-dione (I) and its hydrochloride salt. (A-R=COCH$_2$CHCH$_3$, R$_3$-R$_1$=ONH, Z=

EXAMPLE 61

1-Methyl-4-(3-aminocyclopentyl)-5-fluoro-1,2,8,9-tetrahydro-7H-isothiazolo[4',5':5,6]pyrido[1,2,3-de][1,4]benzoxazine-7,8-dione In the described fashion as Example 52, replacing 1-cyclopropyl-2-methylthio-6-fluoro-7-(4-N-t-carbobutoxyaminocyclohexyl)-1,4-dihydro-4-oxo-quinoline-3-carboxylate (16) (A=CH, R$_{11}$=CH$_3$, R$_{10}$=C$_2$H$_5$, R=cyclopropyl, Z=

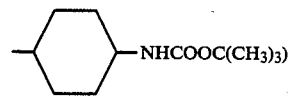

with ethyl 9-fluoro-10-(3-N-t-carbobutoxyaminocyclopentyl)-3-methyl-5-phenylthio-2,3-dihydro-7-oxo-7H-pyrido[1,2,3-de][1,4]benzoxazine-6-carboxylate (16) of Example 59 (A-R=COCH$_2$CHCH$_3$, R$_{10}$=C$_2$H$_5$, R$_{11}$=C$_6$H$_5$, Z=

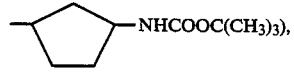

one can obtain 1-methyl-4-(3-aminocyclopentyl)-5-fluoro-1,2,8,9-tetrahydro-7H-isothiazolo[4',5':5,6]pyrido[1,2,3-de][1,4]benzoxazine-7,8-dione (I) and its hydrochloride salt. (A-R=COCH$_2$CHCH$_3$, R$_3$-R$_1$=SNH, Z=

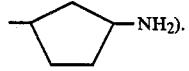

It will be understood that various changes and modifications can be made in the details of procedure, formulation and use without departing from the spirit of the invention, especially as defined in the following claims.

What is claimed is:

1. A compound having the formula:

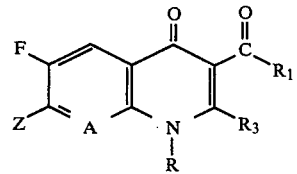

wherein R$_1$ is a hydroxy, a C$_1$ to C$_6$ alkoxy, benzoxy, or a C$_1$ to C$_6$ alkylcarbonyloxymethoxy group; R$_3$ is hydrogen; A is nitrogen; R is (1) a C$_1$ to C$_4$ alkyl, (2) lower cycloalkyl (3) C$_1$ to C$_4$ alkylamino, (4) halo-substituted C$_1$ to C$_4$ alkyl, or (5) a phenyl group of the formula:

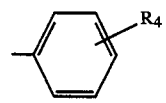

wherein R$_4$ is one, two or three substituents independently selected from hydrogen, halogen, C$_1$ to C$_4$ alkyl, methyldenedioxy, and a group of the formula OR$_5$, wherein R$_5$ is hydrogen or C$_1$ to C$_5$ alkyl; and Z is a carbocyclic group of the formula:

where n is 1 or 2, and R$_7$ is one or more of (1) hydrogen, (2) halogen, (3) loweralkyl, (4) oxo, (5) cyano, (6) C$_1$ to C$_3$ alkanoylamino, (7) carboxyl, (8) nitro, (9) halo-substituted C$_1$ to C$_4$ alkyl, (10) phenyl, (11) a substituted phenyl of the formula:

(12) an amine having the formula:

(13) an aminoalkyl group having the formula:
wherein, m is 1 to 4, $R_8$ and $R_9$ are independently selected from hydrogen, $C_1$ to $C_4$ alkyl, $C_1$ to $C_4$ alkylamino, hydroxy substituted $C_1$ to $C_4$ alkyl, and amino;
or (14) an amine of the formula:

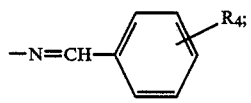

or a pharmaceutically acceptable salt thereof; with the proviso that when $R_1$ is hydroxy, $C_1$ to $C_6$ alkoxy or benzoxy and R is $C_1$ to $C_4$ alkyl, or halo-substituted $C_1$ to $C_4$ alkyl, then Z is other than cyclopentyl, cyclopentyl substituted by loweralkyl, cyclohexyl or cyclohexyl substituted by loweralkyl.

2. A compound defined in claim 1 wherein R is cyclopropyl; $R_1$ is hydroxy, $R_3$ is hydrogen, A is nitrogen; and Z is selected from 3-aminocyclopentyl, 4-aminocyclohexyl and 3-ethylaminomethylcyclopentyl.

3. A compound defined in claim 1, wherein R is ethyl; $R_1$ is hydroxy; $R_3$ is hydrogen; A is N; Z is selected from 3-aminoclopentyl, 4-aminocyclohexyl and 3-ethylaminomethylcyclopentyl.

4. A compound defined in claim 1, wherein R is p-fluorophenyl; $R_1$ is hydroxy, $R_3$ is hydrogen; A is N; Z is selected from 3-aminocyclopentyl, 4-aminocyclohexyl, and 3-ethylaminomethylcyclopentyl.

5. A compound defined in claim 1, wherein R is o,p-difluorophenyl; $R_1$ is hydroxy; $R_3$ is hydrogen; A is N; and Z is selected from 3-aminocyclopentyl, 4-aminocyclohexyl and 3-ethylaminomethylcyclopentyl.

6. A composition having antibacterial activity in pharmaceutical dosage form containing a diluent and a therapeutically effective amount of a compound as defined in claim 1.

7. A method of treating a bacterial infection in a patient comprising administering to a patient in need of such treatment a therapeutically effective amount of a compound as defined in claim 1.

* * * * *

UNITED STATES PATENT AND TRADEMARK OFFICE
CERTIFICATE OF CORRECTION

PATENT NO. : 4,880,814
DATED : November 14, 1989
INVENTOR(S) : Daniel R. Chu, Terry J. Rosen and Curt S. Cooper It is certified that error appears in the above-identified patent and that said Letters Patent is hereby corrected as shown below:

Title page, column 1, line 1, After "NAPHTHYRIDINES," insert --ANTIBACTERIAL COMPOUNDS--

Title page, column 2, line 14, Replace "-X-CH$_2$-CH=CH$_2$" with ---X-CH$_2$-C̱=CH$_2$--.

Title page, column 2, line 23, Delete "1".

Column 2, line 19, After "formula:" insert

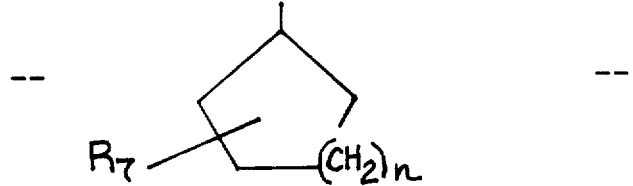

Column 2, line 39, After "formula:" insert

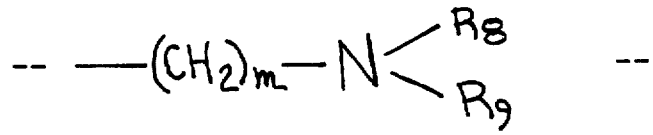

Column 4, line 15, Replace "1-ethyl6" with --1-ethyl-6--.

Column 4, line 44, Replace "[1,8]naphthyridine" with --[1,8]-naphthyridine--.

UNITED STATES PATENT AND TRADEMARK OFFICE
CERTIFICATE OF CORRECTION

PATENT NO. : 4,880,814
DATED : November 14, 1989
INVENTOR(S) : Daniel R. Chu, Terry J. Rosen and Curt S. Cooper It is certified that error appears in the above-identified patent and that said Letters Patent is hereby corrected as shown below:

Column 6, line 6, After "[4',5':5,6 " insert --]--.

Column 6, line 7, Replace "]pyrido" with --pyrido--.

Column 6, line 9, After "[4',5':5,6 " insert --]--.

Column 6, line 10, Replace "]pyrido" with --pyrido--.

Column 6, line 14, After "[4',5:5,6 " insert --]--.

Column 6, line 15, Replace "]pyrido" with --pyrido--.

Column 6, line 17, After "[4',5:5,6 " insert --]--.

Column 6, line 18, Replace "]pyrido" with --pyrido--.

Column 26, line 68, Replace "y" with --by--.

Column 28, line 60, After "(35)" insert --(--.

Column 29, line 44, Replace "(16(a)," with --16(a),--.

Column 48, line 29, Replace "65" with --5--.

UNITED STATES PATENT AND TRADEMARK OFFICE
CERTIFICATE OF CORRECTION

PATENT NO. : 4,880,814

DATED : November 14, 1989

INVENTOR(S) : Daniel R. Chu, Terry J. Rosen and Curt S. Cooper

It is certified that error appears in the above-identified patent and that said Letters Patent is hereby corrected as shown below:

Column 54, line 9, Replace "1,8naphthyridine-3-carboxylate" with --1,8-naphthyridine-3-carboxylate--.

Column 61, line 53, After "[1,4 " insert --]--.

Column 61, line 54, Replace "]benzoxazine" with --benzoxazine--.

Column 62, line 13, After "[4',5':5,6)-" insert --]--.

Column 62, line 14, Replace "]pyrido" with --pyrido--.

Column 62, line 28, After "[1,4 " insert --]--.

Column 62, line 29, Replace "]benzoxazine" with --benzoxazine--.

Column 62, line 58, After "[4',5':5,6 " insert --]--.

Column 62, line 59, Replace "]pyrido" with --pyrido--.

Column 63, line 20, After "NHCOOC(CH3)3)" insert --.--.

Column 63, line 26, After "[1,4 " insert --]--.

Column 63, line 27, Replace "]benzoxazine" with --benzoxazine--.

UNITED STATES PATENT AND TRADEMARK OFFICE
CERTIFICATE OF CORRECTION

PATENT NO. : 4,880,814
DATED : November 14, 1989
INVENTOR(S) : Daniel R. Chu, Terry J. Rosen and Curt S. Cooper It is certified that error appears in the above-identified patent and that said Letters Patent is hereby corrected as shown below:

Column 63, line 51, After "[4',5':5,6 " insert --]--.

Column 63, line 52, Replace "]pyrido" with --pyrido--.

Column 63, line 63, After "[1,4 " insert --]--.

Column 63, line 64, Replace "]benzoxazine" with --benzoxazine--.

Column 64, line 21, After "[4',5':5,6 " insert --]--.

Column 64, line 22, Replace "]pyrido" with --pyrido--.

Column 64, line 62, After "formula:" insert

-- 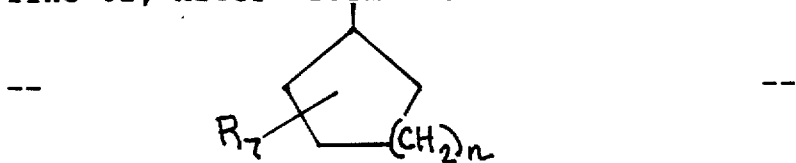 --

Column 64, line 67, After "formula:" insert

-- 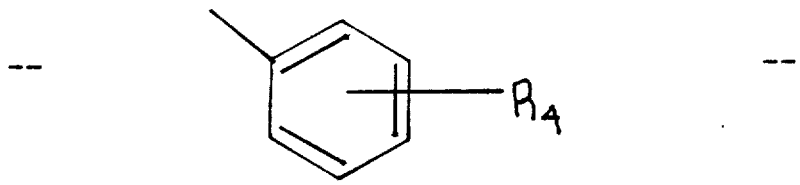 --

UNITED STATES PATENT AND TRADEMARK OFFICE
CERTIFICATE OF CORRECTION

PATENT NO. : 4,880,814

DATED : November 14, 1989

INVENTOR(S) : Daniel R. Chu, Terry J. Rosen and Curt S. Cooper

It is certified that error appears in the above-identified patent and that said Letters Patent is hereby corrected as shown below:

Column 65, line 7, After "formula:" insert

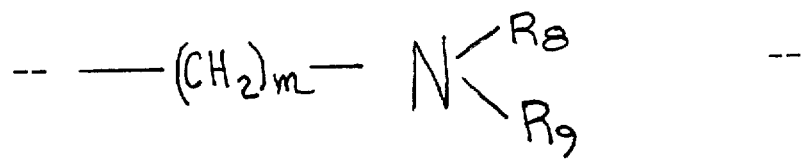

$$-- \quad -(CH_2)_m- \quad N\genfrac{}{}{0pt}{}{R_8}{R_9} \quad --$$

Signed and Sealed this

Fourteenth Day of January, 1992

Attest:

HARRY F. MANBECK, JR.

Attesting Officer      Commissioner of Patents and Trademarks